United States Patent
Nonomura et al.

[11] Patent Number: 6,121,195
[45] Date of Patent: Sep. 19, 2000

[54] METHODS AND COMPOSITIONS FOR ENHANCING FORMYLTETRAHYDRO-PTEROYL POLYGLUTAMATE IN PLANTS

[76] Inventors: Arthur M. Nonomura, 311 Depot Rd., Boxborough, Mass. 01719; John N. Nishio, 519 S. 8th St., Laramie, Wyo. 82070; Andrew A. Benson, 6044 Folsom Dr., La Jolla, Calif. 92037

[21] Appl. No.: 09/207,172

[22] Filed: Dec. 7, 1998

Related U.S. Application Data

[60] Division of application No. 08/610,928, Mar. 5, 1996, Pat. No. 5,846,908, which is a continuation-in-part of application No. 08/399,399, Mar. 6, 1995, abandoned, which is a continuation-in-part of application No. 08/351,348, Dec. 9, 1994, Pat. No. 5,597,400, which is a continuation of application No. PCT/US93/05676, Jun. 14, 1993, which is a continuation-in-part of application No. 07/901,366, Jun. 19, 1992, abandoned.

[51] Int. Cl.[7] .......................... A01N 37/10; A01N 37/18; A01N 43/54; A01N 43/90
[52] U.S. Cl. .......................... 504/136; 504/143; 504/144; 504/147; 504/149; 504/241; 504/318; 504/324; 504/339
[58] Field of Search .................................... 504/136, 143, 504/144, 147, 149, 241, 318, 324, 339

[56] References Cited

U.S. PATENT DOCUMENTS

| | | | |
|---|---|---|---|
| 3,891,756 | 6/1975 | Kasugai et al. | 424/177 |
| 3,897,241 | 7/1975 | Washio et al. | 71/113 |
| 3,918,952 | 11/1975 | Neumiller | 71/28 |
| 3,978,119 | 8/1976 | Onopehenko et al. | 260/523 R |
| 4,033,745 | 7/1977 | Moore | 71/28 |
| 4,383,845 | 5/1983 | Rutherford | 71/16 |
| 4,405,531 | 9/1983 | Franz | 260/501.12 |
| 4,409,015 | 10/1983 | Grace, Jr. | 71/28 |
| 4,594,096 | 6/1986 | Albrecht et al. | 71/93 |
| 4,799,953 | 1/1989 | Danzig et al. | 71/98 |
| 4,863,506 | 9/1989 | Young | 71/113 |
| 5,139,555 | 8/1992 | Freepons | 71/29 |
| 5,549,729 | 8/1996 | Yamashita | 71/26 |

FOREIGN PATENT DOCUMENTS

| | | |
|---|---|---|
| 1046886 | 11/1990 | China . |
| 244754 | 11/1987 | European Pat. Off. . |
| 465907 | 1/1992 | European Pat. Off. . |
| T45468 | 7/1988 | Hungary . |
| 62-28117 | 6/1987 | Japan . |
| 93/4341 | 3/1994 | South Africa . |
| 816437 | 4/1981 | U.S.S.R. . |
| 1289866 | 2/1987 | U.S.S.R. . |
| 2004856 | 4/1979 | United Kingdom . |
| 2185472 | 7/1987 | United Kingdom . |
| 94/00009 | 1/1994 | WIPO . |

OTHER PUBLICATIONS

H.Aono et al., Effect of foliar application of fertilizer on the growth and quality of new shoot of tea plant, Nat'l. Res. Inst. Tea, 63:23–32 (1982).

D.Barel et al., Foliar application of P.II. yield responses of corn and soybeans sprayed with various condensed phosphates and P–N compounds in greenhouse and field experiments, Agronomy Journal, 81(1): 21–24 (1979).

A. Benson, Identification of ribulose in C1402 photosynthesis products, J. Am. Chem. Soc., 73:2971 (1951).

V. Besson et al., Effects of tetrahydrofolate polyglutamates on the kinetic parameters of serine hydroxymethyltransferase and glycine decarboxylase from pea leaf mitochondria, Biochem. J., 292:425–430 (1993).

(List continued on next page.)

*Primary Examiner*—S. Mark Clardy
*Attorney, Agent, or Firm*—Nields, Lemack & Dingman

[57] ABSTRACT

Methods and compositions for enhancing plant growth provide for foliar application of a substance which enhances the accumulation of formyltetrahydropteroyl polyglutamate ($C_1$-THF) in a treated plant. Treatment with substances that contribute to the structure of $C_1$-THF increase the rate and quantity of carbon fixation by the plant. Thereafter, plant growth is further improved either by exposure of the plant to elevated oxygen, illumination and heat or by foliar input of single carbon fragment sources. Optimal results are obtained by combined treatment with a substance that can serve as a sink for $C_1$ fragments produced in the leaf.

21 Claims, 10 Drawing Sheets

OTHER PUBLICATIONS

Chemistry and Biology of Pteridines and Folates, Edited by J.Ayling et al., Plenum Press, New York, NY/ pp. 1–16 (1993).

C.Cooney et al., Microbial utilization of methanol, Adv. in Applied Microbiology, 15:337–365 (1972).

E. Cossins, Folate biochemistry and the metabolism of one–carbon units, The Biochemistry of Plants—vol. 11, Academic Press. pp. 317–353 (1987).

E. Cossins, One–carbon metabolism, The Biochemistry of Plants—vol. 2, Academic Press, pp. 365–418 (1980).

E. Cossins, The utilization of carbon–1 compounds by plants, Canadian J. Biochem., 42:1793–1802 (1964).

P. Crosti et al., Growth–dependent changes of folate metabolism and biosynthesis in cultures Daucus–carota cells, Plant Science, 88:97–106 (1993).

R. Gates et al. Free amino acids exhibit anthozoan "host factor" activity: They induce the release of photosynthate from symbiotic dinoflagellates in vitro, Proc. Nat'l. Acad. Sci, USA, 92:7430–7434 (Aug. 1995).

T. Gorontzy et al., Microbial transformation of nitroaromatic compounds under anaerobic conditions, J. General Microbiol., 139:1331–1336 (1993).

H. Grassi Filho et al., Effect of calcium, boron, molybdenum, and zinc on the dry–matter yield of soybeans, Rev. Agric. (Brazil), 67(1):89–95 (1992).

B.Grodzinski, Glyoxylate decarboxylation during photorespiration, Planta, 144:31–37 (1978).

A. Gupta et al., Metabolism of N–(4–Chloro–o–tolyl)–N, N–dimethylformamidine by apple seedlings, J. Agr. Food Chem., 17(3) :595–600 (1969).

W.Harder et al., Methanol assimilation by Hyphomicrobium sp., J. General Microbiol., 78:155–163 (1973).

S.Kannan, Effects of dibutyl phthalate and phthalic acid on chlorosis recovery in iron–deficiency stressed sorghum cultivars, J. Plant Nutrition, 9(12): 1543–1551 (1986).

V.Kazaryan et al., On the influence of nitrogen nutrition on the growth intensity and balance of physiologically active substances in separate organs of sunflower and lilac, Biol. Zh. Arm., 42(3): 177–181 (1989).

J. Killmer, Growth of cultured carrot cells as affected by glyphosphate, asulam and various plant metabolites, Graduate Thesis—University of Illinois, (1980).

C. Knowles, Metabolism of two acaricidal chemicals, N–(4–Chloro–0–tolyl) –N,N–dimethylformamidine (chlorphenamidine) and m–{[(Di–methylamino)methylene]amino}phenyl methylcarbamate hydrochloride (formetanate), J. Agr. Food Chem., 18(6):1038–1047 (1970).

H.Kruschwitz, 5–Formyltetrahydropteroylpolyglutamates are the major folate derivatives in Neurospora crassa conidiospores, J. Biol. Chem., 269(46): 28757–28763 (1994).

A.Lawyer et al., Glyoxylate and glutamate effects of photosynthetic carbon metabolism in isolated chloroplasts and mesophyll cells of spinach, Plant Physiol., 72:420–425 (1983).

J.Nishio et al., Changes in thylakoid galactolipids and proteins during iron nutrition–mediated chloroplast development, Plant Physiol., 77:705–711 (1985).

W.Ogren, Photorespiration: pathways, regulation, and modification, Ann. Rev. Plant Physiol., 35:415–442 (1984).

D.Oliver et al., Increasing photosynthesis by inhibiting photorespiration with glyoxylate, Science, 196; 1450–1451 (1977).

D.Oliver et al., Metabolic regulation of glycolate synthesis, photorespiration, and net photosynthesis in tobacco by L–glutamate, Plant Physiol., 59:688–694 (1977).

A.Pavlova et al., Influence of leaf feeding on 14C–proline uptake by forming wheat grain, Dokl. Bolg. Akad. Nauk., 39(3): 101–103 (1986).

J.Quayle et al., Enzymatic Carboxylation of Ribulose Diphosphate, J. Amer. Chem. Soc., 76:3610–3611 (1954).

A. Schackmann et al., Reduction of nitroaromatic compounds by different pseudomonas species under aerobic conditions, Appl. Microbiol. Biotechnol., 34:809–813 (1991).

S. Schuler et al., Nitrogen nutrition and growth regulator effects of oxamide on what and soybean, J. Plant Nutrition, 11(2) :217–233 (1988).

P. Stover et al., Evidence that 5–formytetrahydropteroyl–glutamate has a metabolic role in one carbon metabolism, Chem. and Biol. of Pteridiens and Folates, Edited by J. Ayling et al., Plenum Press New York, NY, pp. 679–685 (1993).

N.Tolbert, Formic acid metabolism in barley leaves, J. Biol. Chem., 215:27–34 (1955).

C. Wendler et al., Effect of glufosinate (phosphinothricin) and inhibitors of photorespiration on photosynthesis and ribulose–1,5–biphosphate carboxylase activity, J. Plant Physiol., 139:666–671 (1992).

Western Fertilizer Handbook, Edited by G.Hawkes et al., Soil Improvement Committee of California Fertilizer Association, pp. 55–81 (1985).

J. Wu et al., Photorespiration is more effective than the Mehler reaction in protecting the photosynthetic apparatus against photoinhibition, Bot. Acta. 104:283–291 (1991).

I.Zelitch, Effect of glycidate, an inhibitor of glycolate synthesis in leaves, on the activity of some enzymes of the glycolate pathway, Plant Physiol., 61:236–241 (1978).

I.Zelitch, The photooxidation of glyoxylate by envelopefree spinach chloroplasts and its relation to photorespiration, Archives of Biochem. and Biophys., 150:698–707 (1972).

METHODS AND COMPOSITIONS FOR ENHANCING FORMYLTETRAHYDRO-PTEROYLPOLYGLUTAMATE IN PLANTS

This application is a division of U.S. patent application Ser. No. 08/610,928, filed Mar. 5, 1996, now U.S. Pat. No. 5,846,908, which is a continuation-in-part of U.S. patent application Ser. No. 08/399,399, filed Mar. 6, 1995 now abandoned which was a continuation-in part of U.S. patent application Ser. No. 08/351,348, filed on Dec. 9, 1994, now U.S. Pat. No. 5,597,400 which was filed as a continuation under 35 USC 371 of PCT International Application PCT/US93/05676, filed on Jun. 14, 1993, which was a continuation-in-part of application Ser. No. 07/901,366, filed on Jun. 19, 1992 now abandoned. The full disclosures of each of these patent applications are incorporated herein by reference.

BACKGROUND OF THE INVENTION

1. Field of the Invention

The present invention relates generally to methods and compositions for stimulating carbon nutrient uptake that yields enhanced growth in plants with improved water use efficiency.

Photosynthesis is the process by which all photosynthetic plants utilize solar energy to build carbohydrates and other organic molecules from carbon dioxide ($CO_2$) and water. The conversion of $CO_2$ into plant matter is generally referred to as carbon fixation and occurs by the $C_3$ cycle in most plants. Plants in which the $C_3$ cycle occurs are referred to hereinafter as "$C_3$ plants". The $C_3$ cycle involves the carboxylation of ribulose-1,5-bisphosphate (RuBP) to produce two molecules of the 3-carbon compound, 3-phosphoglyceric acid (PGA), the carbon skeleton for hexoses and other organic molecules. An important aspect of the $C_3$ cycle is that the RuBP pool remains charged during carbon uptake. Therefore, for every six carboxylation events, which yields twelve PGA's, two PGA's can be converted to hexose, while ten molecules of PGA are recycled to replace the six RuBP's initially carboxylated. A simplified illustration of the $C_3$ cycle is shown in FIG. 1.

Another event in the $C_3$ cycle shown in FIG. 1, is photorespiration, during which oxygen ($O_2$) outcompetes $CO_2$ and is added to RuBP. As a result of oxidation, phosphoglycolate is formed. The phosphoglycolate is dephosphorylated to glycolate which is oxidized to glyoxylate. Glycine is made by attachment of ammonia ($NH_3$). The glycine is deaminated releasing $NH_3$ and further decarboxylated to $CO_2$ plus a single carbon ($C_1$) fragment. This $C_1$ fragment from glycine is passed on to a FORMYLTETRAHYDROPTEROYLPOLYGLUTAMATE ($C_1$-THF) pool, whereby, it is catalytically transferred in the form of 5,10-methylenetetrahydrofolate. Serine hydroxymethyltransferase (SHMT), an abundant enzyme of the $C_1$-THF pool, reversibly catalyzes the attachment of a second molecule of glycine with the $C_1$ fragment to make serine. Photorespiration is a source of glyoxylate which is ultimately cleaved into $C_1$ fragments.

The amination of glyoxylate and deamination of glycine during photorespiration occurs through the GOGAT (glutamine: 2-oxo-glutarate amino transferase) cycle. The GOGAT cycle is the path by which $NH_3$ is assimilated by plants and follows the depiction given in FIG. 2, wherein, glutamine: 2-oxo-glutarate amino transferase catalyzes the combining of glutamine with 2-oxo-glutarate to form two molecules of glutamate. In the course of photorespiration, one molecule of glutamate can provide $NH_3$ for amination of glyoxylate to form glycine, while the other is recycled and combines with the $NH_3$ released when glycine is deaminated, as shown in FIG. 2. In another energy consuming process, the serine formed must be recycled back to the RuBP pool for further carboxylations, otherwise photorespiration would drain the RuBP pool. Recycling serine to PGA involves an amino transfer from serine to glyoxylate to form glycine. The resulting 1-hydroxypyruvate is reduced to glycerate and then phosphorylated to form PGA. The PGA can be recycled back to RuBP. The energy intensive process of photorespiration depletes $C_2$ and releases $CO_2$ but salvages 75% of the carbons in the glycolate produced.

Conventional plant nutrient formulations have been directed at the delivery of recognized macro- and micronutrients, but have not generally included a carbon source intended to enhance carbon dioxide fixation by the $C_3$ cycle or otherwise, as defined by Hawkes et al. (1985) *Western Fertilizer Handbook*, The Interstate Publishers, Danville, Ill., Pp. 288. Fertilizers for higher plants generally include nitrogen, phosphorus, and potassium, which are referred to as macronutrients. Fertilizers often include other minerals and micronutrients, such as, iron, sulfur, calcium, and magnesium, which may support growth if there is a deficiency; but they are not utilized to target enhancement of catalysts that would divert from conventional pathways. The use of conventional fertilizers to enhance plant growth via the $C_3$ cycle is inefficient and incomplete because photosynthesis under normal atmospheric conditions is $CO_2$-limited and light-limited. A fertilizer that provides carbon, enhances uptake of carbon, or increases the efficiency of carbon metabolism would increase growth. Conventional fertilizers do not directly provide carbon as a nutrient nor do they improve carbon fixation even though carbon accounts for 80% or more of plant growth under the conventional $C_3$ cycle. Because of their imbalances, application of conventional fertilizers has never achieved optimal productivity during photorespiration.

For these reasons, it would be desirable to provide improved methods and formulations for promoting plant growth. It would be particularly desirable if such methods and compositions were able to maintain flows of $C_1$ fragments which enhance growth without toxicity. The present invention should further provide convenient methods resulting in increased photosynthesis for applying the compositions to photosynthetic plant surfaces. Additionally, it would be desirable if the methods and compositions of the present invention could promote rapid growth and maturing of the treated plant, increase sugar content and, otherwise, increase the quality of the plant, all the while, adjusting transpiration to reduce the watering requirement of the plant and enhance environmental tolerance.

2. Description of the Background Art

Study of the path of carbon in photosynthesis four decades ago (A. A. Benson (1951) "Identification of Ribulose in $^{14}CO_2$ Photosynthesis Products" *J. Am. Chem. Soc.* 73:2971; J. R. Quayle et al. (1954) "Enzymatic Carboxylation of Ribulose Diphosphate" *J. Am. Chem. Soc.* 76:3610) revealed the nature of the $CO_2$ fixation process in plants. The metabolism of one-carbon compounds other than $CO_2$ had been examined, and methanol was found to be utilized by algal strains of Chlorella and Scenedesmus for sugar and amino acid production as rapidly as $CO_2$. Since both types of early experiments were performed with substrate on a tracer scale, it was neither clear that the rates were comparable nor what the pathway for methanol conversion to sucrose involved. A subsequent publication on the subject (E. A. Cossins (1964) "The Utilization of Carbon-1 Compounds by Plants" *Canadian. J. Biochem*. 42:1793) reported that plants metabolize methanol to $CO_2$, glycerate, serine, methionine, and other sugar or structural precursors rapidly. The conclusion that methanol is readily oxidized to formaldehyde and converted to fructose-6-phosphate has been reported in bacteria (C. L. Cooney and D. W. Levine (1972) "Microbial Utilization of Methanol" *Adv. Appl. Microbiol.* 15:337) and fungi (W. Harder et al. (1973) "Methanol Assimilation by Hyphomicrobium sp." *J. Gen. Microbiol.* 78:155). Based on these studies of microorganisms it was concluded that formaldehyde condenses with pentose-5-phosphate to yield allulose-6-phosphate which epimerizes to fructose-6-phosphate.

$C_1$ metabolism in higher plants is discussed in Cossins, "One-carbon Metabolism", *The Biochemistry of Plants*, Vol. 2, Ch. 9, Pp. 365–418, Academic Press, Inc., 1980, and in Cossins, "Folate Biochemistry and the Metabolism of One-Carbon Units," *The Biochemistry of Plants*, Vol. 11, Ch. 9, Academic Press, Inc., 1987. In his review of photorespiration, W. L. Ogren (1984), "Photorespiration: Pathways, Regulation, and Modification." *Ann. Rev. Physiol*. 35:415–442, concludes that accumulation of glycolate inhibits plant growth; and furthermore, chemical or genetic inhibition of the glycolate pathway leads to plant death.

Additions of folic acid, pteroic acid, methyltetrahydrofolate and folinate to root cell culture nutrient medium, as described by P. Crosti, M. Malerba and R. Bianchetti (1993) "Growth-dependent changes of folate metabolism and biosynthesis in cultured Daucus-carota cells," *Plant Science* 88(1):97–106, shows that growth was inhibited by folinate, aminopterin, methotrexate and sulfanilamide; and even though initial rates of growth were stimulated by folic acid, inhibited by pteroic acid, or were unaffected by methyltetrahydrofolate, the final growth yield was no different from the untreated control in any case.

J. Killmer, Ph.D. Thesis entitled *Growth of Cultured Carrot Cells as Affected by Glyphosate, Asulam, and Various Plant Metabolites*, University of Illinois, Urbana-Champaign, 1980, describes the effect of metabolites, including p-aminobenzoic acid (pABA) and folate, when applied to plants together with the herbicide glyphosate. Both pABA and folate were applied to plants as controls with no effect on growth being observed.

Foliar fertilizers containing calcium formate are described in Japanese Patent Publication 59-137384. U.S. Pat. No. 3,897,241 describes application of ethanolamine formulations with carboxylic acids of less than 8 carbons, such as, oxalic acid, formic acid, acetic acid, phthalic acid and glutaric acid to fruit-bearing plants 10 to 150 days prior to ripening. European Patent 465 907 A1 describes compositions for stimulating the growth and ripening of plants comprised of at least one adduct of menadione bisulfite and a compound chosen from a group including pABA. U.K. Patent Application 2 004 856 describes plant growth stimulating compositions consisting of cysteine as the active component in formulations that also include folic acid, an aldehyde, a magnesium salt, and a buffer. U.S. Pat. No. 4,405,531, discloses the novel derivatives of N-phosphonomethylglycine used as phytotoxicants and herbicides. USSR application 816437 describes the spraying of cucumber leaves with glutamic acid to accelerate fruit maturation and increase crop yield. Lawyer et al. (1983) *Plant Physiol*. 72:420–425 describes glutamate addition to chloroplasts having no effect on net photosynthesis of chloroplasts, but increasing $^{14}CO_2$ incorporation on addition to isolated spinach cells; furthermore, they also concluded, that treatment with sodium glyoxylate inhibits photosynthesis. Grassi et al. (1992) *Rev. Agric.* 67:89–95, describes the foliar application of amino acids to enhance the growth of soybeans. Aono et al. (1982) *Chagyo Gijutsu Kenkyu* 63:23–32, describes the spraying of tea plants with vitamins and amino acids to enhance yield. Kazaryan et al. (1989) *Biol. Zh. Ann.* 42:177–181, describes the foliar spray of glycine to induce auxin and growth inhibitor production in nitrogen-deprived plants. Chinese patent application 1046886 describes plant leaf fertilizers including amino acids.

Methanol and other alcohols have been included in certain prior fertilizer formulations for various purposes. U.S. Pat. No. 3,918,952, discloses the incorporation of 1–15 parts by volume lower alcohol in clear liquid fertilizers as stability enhancers. U.S. Pat. No. 4,033,745, discloses the incorporation of 0.05% to 1% alcohol in liquid fertilizers as a stability enhancer. U.S. Pat. Nos. 4,409,015 and 4,576,626 describe the addition of alcohols to fertilizers to enhance solubilization of phospholipids. See also Hungarian patent abstract T45468 and USSR patent abstract 84-3794472, which describes the incorporation of methanol into fertilizers at unspecified concentrations.

British patent application 2 185 472 A describes foliar plant feeding compositions which comprise from 2% to 4% by weight of protein hydrolysate including amino acids, polypeptides, and oligopeptides. Particular amino acids are not identified. The application of oxamide ($H_2N$—CO—CO—$NH_2$) in foliar sprays to wheat and soy as a slow-release of nitrogen source is described in Schuler and Paulsen (1988) *J. Plant Nutr*. 11:217–233. The foliar application of radiolabeled proline to wheat is described in Pavlova and Kudrev (1986) *Dolk. Bolg. Akad. Nauk.* 39:101–103. Barel and Black (1979) *Agron. J.* 71:21–24 describes foliar fertilizers incorporating polyphosphate compounds combined with a surfactant (0.1% Tween® 80). U.S. Pat. No. 4,863,506, describes the incorporation of L-(d)-lactic acid in foliar sprays where the lactic acid is alleged to act as a growth regulator. U.S. Pat. No. 4,799,953, describes polymeric condensates of the sulfur-polymers, thiolactic and thioglycolic acids, increasing the rate of growth and chlorophyll specific to tissue and hydroponic culture of *Lemna minor*.

The degradation of formamidine-derivative insecticides in plants has been variously described by C. O. Knowles (1970) *J. Agr. Food Chem.* 18:1038–1047 for chlordimeform; C. D. Ercegovich, S. Witkonton and D. Asquith (1972)) *J. Agr. Food Chem.* 20:565–568 and A. K. Sen Gupta and C. O. Knowles (1986) *J. Agr. Food Chem.* 17:595–600 for chlordimeform and formetanate. R. T. Meister (1995) Editor-in-Chief, *Farm Chemicals Handbook*, Meister Publishing Co., Willoughby, OH, describes several commercial formamidine insecticides.

R. T. Meister, supra, describes limited use of phthalates as pesticides; for example, European Patent 244,754/EP was granted for herbicides emulsified in water-immiscible mixtures that can include a phthalate; U.S. Pat. No. 4,594,096 describes pesticides containing alkyl phthalate as a solvent; U.S. Pat. No. 3,891,756 describes pesticidal compositions that contain a starchy biopolymer, a carbonate and an organic acid, among which phthalic acid was included. Root treatments of phthalate derivatives for iron deficiency is described in a research series by S. Kanan, for example, S. Kanan (1986) *J. Plant Nutrition* 9(12):1543–1551, shows phthalic acid and dibutyl phthalate can reverse chlorosis in sorghum.

PCT WO94/00009 is the published text of parent application PCT/US93/05673 (published on Jan. 6, 1994). South African patent 93/4341, which is also the equivalent of PCT/US93/05673, issued on Mar. 30, 1994.

SUMMARY OF THE INVENTION

According to the present invention, methods and compositions are provided for stimulating carbon fixation and increasing the growth of plants by enhancing the availability of $C_1$-THF in the leaves of a plant. As shown in FIG. 6, the $C_1$-THF molecule can be segmented into distinct components including a formylpteroyl glutamide (the example shown in FIG. 6 is folinate carrying multiple glutamates) and a polyglutamate ($Glu_n$) chain. The formylpteroyl glutamide can be further subdivided into a $C_1$-fragment, a pteridine and an aminobenzoylglutamic acid. Foliar application of substances that increase the amount of $C_1$-THF, either by contributing any one of these components to the structure of $C_1$-THF or otherwise promoting the formation of $C_1$-THF, increases carbon fixation by the $C_1$ pathway and enhances plant growth. Such substances which increase the amount of $C_1$-THF in the leaf of a plant are referred to herein as "enhancers" or "enhancer substances".

As provided herein, an enhancement of the carbon pathway focuses on modulating the flow of carbon through $C_1$-THF in a manner that enhances fixation of $C_1$ fragments in plants. $C_1$-THF is a catalyst for $C_1$ metabolism, meaning that $C_1$ metabolism is dependent upon $C_1$-THF. By adding to the $C_1$-THF content of a leaf, catalysis of $C_1$ fragments is enhanced, i.e., the plant's capacity to metabolize $C_1$-fragments by increasing the flow of carbon through the $C_1$-THF pool and thereby fix carbon into cellular constituents is increased proportionately. If the level of $C_1$ fragments is then increased, this then results in increased plant growth according to this newly afforded capacity to metabolize what otherwise would have remained an under-utilized carbon source. This flow, which we refer to as the $C_1$ pathway, is illustrated in FIGS. 4 and 5. The $C_1$ pathway is characterized by passage of $C_1$ fragments to $C_1$-THF, as described by Cossins (1980) and (1987), infra. When addition of a fertilizer having the components disclosed herein enhances the catalyst, $C_1$-THF, i.e., by increasing the formyltetrahydropteroylpolyglutamate pool, improved carbon fixation, water use efficiency and plant growth results. The level of $C_1$ fragments may be increased by exposure to appropriate environmental conditions or by the addition of substances which are capable of being metabolized to $C_1$ fragments. All such substances are referred to as "$C_1$-input substances".

Organic compounds can find passage through $C_1$-THF as a consequence of the metabolism of much larger molecules from which $C_1$ fragments arise. For example, the incorporation of formimino-amino acids is illustrated in FIGS. 4 and 5, wherein, a $C_1$ fragment is transported as formiminotetrahydrofolate. In fact, $C_1$-THF is involved in manners illustrated in FIGS. 4 and 5, representing modifications from Besson et al (1993) and Cossins (1980) and (1987), infra. A supramolecular complex in this scheme is thought to be a storage product, serine hydroxymethyltransferase·glycine·folyl-polyglutamate. Within a leaf, such ternary complexes may be the natural selection for storage because of stability. Modulation of release permits control of the flow of $C_1$-THF, glycine and SHMT. Based on the storage of the ternary complex, treatments are directed towards stimulating its conversion to maintain a high flow of carbon.

The energy consumptive GOGAT cycle can be circumvented if, for instance, glyoxylate were to undergo decarboxylation in a manner depicted in FIG. 3. The remaining $C_1$ fragment, formate, is incorporated through the intermediacy of the $C_1$-THF pool by its addition to glycine yielding serine which is ultimately converted to cellular constituents. Direct fixation of $CO_2$ to formate is known—e.g., S. S. Kent (1972) "Photosynthesis in the higher plant Vicia faba. II. The non-Calvin cycle origin of acetate and its metabolic relationship to the photosynthetic origin of formate," *J. Biol. Chem.* 247:7293–7302; or Ramaswamy et al. (1976) "A novel pathway for the synthesis of solanidine in the isolated chloroplast from greening potatoes," *Eur J Biochem* 67:275–282—and may provide an additional source of $C_1$ units. Therefore, $CO_2$ released from glyoxylate could be refixed via this direct pathway which is much more energy efficient. As can be deduced from FIG. 3, an absolute requirement for circumventing the GOGAT cycle is a source of glycine. In both cases shown in FIGS. 1 and 3, the flow of carbon during photorespiration is dependent on $C_1$-THF and glycine. Furthermore, when fixed carbon, such as, glutamine or glycolate, is added to a leaf, the carbons of serine no longer need to be recycled back to RuBP because the added carbon compensates for those normally lost to glycolate. In fact, even the sole addition of nitrogen in the form of nitrate or $NH_3$ could influence carbon partitioning since energy for nitrogen cycling and serine recycling would be reduced. Thus, both carbon and nitrogen metabolism are interdependent with $C_1$-THF central to their flow. It follows, that when $C_1$-THF is enhanced, the flow of carbon into growth of the plant can also be accelerated. Following enhancement of $C_1$-THF, input of compounds that release $C_1$ fragments or exposure to conditions that produces a flow of glycolate within leaves (thus providing a source of formate for the $C_1$-THF pool as shown in FIG. 3) leads to improved efficiencies of carbon fixation. As a consequence, plant growth improves.

Exposure of the plant to enhancers and conditions which increase the level of $C_1$ fragments, e.g., $C_1$ sources, such as glycolate or carbon inputs leading to formate and formaldehyde, can lead to toxicity and leaf burn as a result of the build up of excess formate. Therefore, substances which serve as a sink for such $C_1$ fragments must normally be provided. Such substances which serve as a sink for $C_1$ fragments in the plant are referred to herein as "$C_1$-acceptor compounds", i.e., they serve as acceptors for $C_1$ fragments which would otherwise be converted to toxic metabolites. These substances can be provided either as part of the enhancer substance or as a separate substance. Frequently, these $C_1$-acceptor compounds are sources of polyglutamate. $C_1$-acceptor compounds may also be glycine or substances that may be metabolized to glycine. Glycine serves as a sink for $C_1$ fragments by being converted to serine which is ultimately converted to sugars and other cellular constituents. $C_1$-acceptor compounds, therefore, provide a means of feeding carbon into the leaves at much higher concentrations than would be possible in their absence. Alternatively, $C_1$-acceptor compound sources may include exposure of the plant to environmental conditions which increase polyglutamate levels using existing plant constituents, but this reliance on natural sources lends itself to inconsistency. Most direct $Glu_n$ chain-lengthening sources, such as glycine, will decrease plant growth when applied alone; but when applied in combination with enhancer substance(s), they increase plant growth.

Highest potency is achieved by foliar application of formulations which provide all the components of $C_1$-THF or readily metabolized precursors thereto, i.e., a $C_1$ fragment, a pteridine, an aminobenzoic acid and a glutamate, or metabolic precursors thereto. For example, when folinate is applied to foliage as an active component formulated with a $Glu_n$ source, the folinate is active at minute micromolar ($\mu$M) concentrations. In contrast, mere application of single carbon sources such as methanol and formate require molar (M) concentrations as much as a million times greater than folinate to show activity.

Folinate has the components of the $C_1$-THF molecule "preassembled" as a formylpteroyl glutamide. It is not necessary that the compositions disclosed herein be preassembled in this fashion. Combinations of substances that contribute to one or more of the previously identified components of the structure of $C_1$-THF also promote plant growth. For example, pteridines formulated with aminobenzoates and $Glu_n$ sources would provide the components for the plant to assemble an entire $C_1$-THF. Alternatively, p-aminobenzoylglutamate may be applied as a single active component, leaving the plant to produce and attach a pteridine. The $C_1$-THF structure may be segmented even further into additional components. For example, the formulation may comprise two compounds such as pABA and potassium glutamate. In this case, the plant would not only be left to produce and attach a pteridine, but it would have to attach the pABA to the glutamate. Thus, there are several components and combinations thereof which may be formulated together for application to foliage to enhance $C_1$-THF and thereby promote plant growth. As used herein, the term "$C_1$-THF" refers to tetrahydrofolates carrying a one-carbon unit. The one-carbon unit can be carried in various oxidation states. In the most reduced form, it is carried as a methyl group. In more oxidized forms, it is carried as a formyl, formimino, or methenyl group. Tetrahydrofolate is also called tetrahydropteroylglutamate ($H_4$PteGlu), see "Biochemistry" by Lubert Stryer, pp. 719–721 (W. H. Freeman, 4th ed. (1995)). The terms "$C_1$-THF", "$C_1$-THF pool(s)" and "tetrahydrofolate pool(s)" as used herein also includes such species that carry more than one glutamate residue, e.g., $C_1$-$H_4$PteGlu$_n$. We refer to compounds capable of contributing components to the molecular structure of the formylpteroylglutamate portion (i.e., $C_1$-$H_4$PteGlu$_n$) of the $C_1$-THF molecule as "enhancers".

Increasing the level of $C_1$-THF as described above gives the plant a greater capacity to fix carbon by the $C_1$ pathway. This capacity is then exploited by treatment of plants with substances which can be utilized by $C_1$-THF as $C_1$ fragments or by exposure of the plants to environmental conditions which increase the flow of $C_1$ fragments into and through the $C_1$-THF pool. Such substances utilizable by $C_1$-THF as $C_1$ fragments may be $C_1$ fragments themselves, e.g., formate, or may be substances which are metabolized to a $C_1$ fragment. All such substances are collectively referred to as "$C_1$-input substances". Environmental conditions which promote the flow of $C_1$ fragments into the $C_1$ pathway are generally those which promote oxidative metabolism of photorespiration, i.e., the photorespiratory cycle initiated by the oxygenase activity of RuBP carboxylase/oxygenase (Rubisco). These conditions are generally referred to as $O_2$-Uptake conditions. Exposure of plants to high levels of $C_1$-input substances and/or $O_2$-Uptake levels alone can be toxic because of buildup of intermediates to toxic levels and because of consumption of products of photosynthesis. Therefore, as described earlier, enhancers and $C_1$-acceptor compounds are supplied to route consumption of photosynthetic products back into synthesis of sugar.

Enhancer substances are generally $C_1$-THF, pteridines, pterins, pteroic acids, pteroyl derivatives, folinates, substituted benzoic acids, substituted benzoates and derivatives thereof; and salts, hydrates and surfactant-linked derivatives thereof. Typically, the enhancer is applied as an aqueous solution at a concentration in the range from about 0.0001% to 0.5%, preferably from about 0.0001 to 0.1%.

Suitable pteridine compounds contribute to the structure of $C_1$-THF and are represented by the formula below wherein:

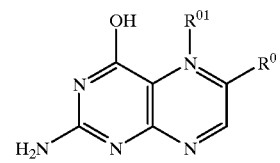

$R^{01}$ is hydrogen or is a hydrocarbyl group capable of being metabolized to a one carbon substituent having the oxidation state of a methyl, hydroxymethyl, formyl or formic acid residue; and $R^0$ is independently selected from the group consisting of: methylene-aminobenzoate, optionally substituted on the benzoate ring; methylene-aminobenzoyl(Glu)$_n$, wherein n is an integer from 0 to 10, optionally substituted on the benzoyl ring; and its corresponding dihydro- and tetrahydro-reduction products at positions 5, 6, 7, and/or 8 of the pteridine rings; and salts, hydrates and surfactant-linked derivatives thereof.

Suitable substituted benzoates contribute to the structure of $C_1$-THF and are represented by the formula below, wherein:

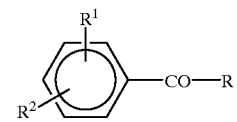

R is H, hydrocarbyl, halogen; —OH; —SH, $NH_2$, N-linked amino acid, N-linked polypeptide, —$OR^3$, —$SR^3$, $NHR^3$, wherein $R^3$ is selected from the group consisting of optionally substituted hydrocarbyl, alkyl, acyl, amino acids or polypeptide chains, —$NR^4R^5$ wherein $R^4$ and $R^5$ which may be the same or different are independently selected from the group consisting of H, optionally substituted hydrocarbyl, alkyl, aryl, acyl, C-terminal linked amino acids, C-terminal linked polypeptide chains, or $R^4$ and $R^5$ together with the nitrogen atoms to which they are linked form a heterocyclic ring;

$R^1$ and $R^2$ are independently selected from the group consisting of:
optionally substituted hydrocarbyl groups, alkyl, aryl, acyl, aroyl, halo, cyano, thio, hydroxy, alkoxy, aryloxy, amino, alkylamino, aminoalkyl, arylamino, aminoaryl, acylamino, ureido, alkylureido, arylureido, hydrazino, hydroxamino, alkoxycarbonylamino, aryloxycarbonylamino, nitro, nitroso, carboxy, alkoxycarbonyl, aryloxycarbonyl, aminocarbonyl, carboxamido, monoalkylaminocarbonyl, dialkylaminocarbonyl, formyl, sulfo, sulfamoyl, sulfoamino, alkylsulfonyl, arylsulfonyl, sulfeno, sulfino, alkylsulfino, arylsulfino; and salts thereof.

In specific cases, acidic enhancers may have very low solubility in cool water (25° C.) and, therefore, require solubilization. For example, pteroic acid, pteroyl(Glu)$_n$ and substituted benzoates, do not dissolve at sufficiently high concentrations in water to promote plant growth. However, they are sufficiently soluble in acids such as formic acid and acetic acid, alcohols such as methanol, alkali metal and alkaline earth metal bases such as potassium hydroxide and calcium hydroxide and carbonates to be formulated in aqueous solution with these agents. Such formulations permit dissolution of the enhancer and facilitate penetration of the enhancer into the leaf of the plant. This then allows enhancement of $C_1$-THF levels in the leaf and promotion of plant growth. Some of the enhancers are activated by dissolving high concentrations in small volumes of alkali followed by adjusting to Ph 7 prior to formulation into aqueous solutions. Solubilizers which aid dissolution of the enhancer and facilitate its penetration into the leaf are referred to as "Activators". Preferred Activators are potassium hydroxide for aminobenzoic acids; normal potassium bicarbonate for folates and phthalic anhydrides; hexamethylenetetramine for pteroic acid; methanol for nitrobenzoic acids; and dimethylsulfoxide (DMSO) for terephthalates.

The $C_1$-input substance for foliar application is usually selected from the group consisting of components that contribute $C_1$ fragments to the $C_1$-tetrahydrofolate pool. Generally, any carbon-containing substance which can be metabolized by any of the metabolic pathways in the leaf to generate a $C_1$ fragment which can be utilized by $C_1$-THF in the $C_1$ pathway can serve as a $C_1$-input substance. $C_1$-input substances include formimino-, methyl-, methenyl-, methylene- and formyl-fragment sources. Examples include, but are not limited to formamidine salts of carboxylic acids, N-formyl amino acids, formimino amino acids, carboxylic acids, aldehydes, trialkyl orthoesters, N-formylated organic compounds and carbon dioxide. Formimino-fragments can originate from formimino-amino acids, purines, histidines, thymidylates and S-adenosylmethionine all of which are metabolized to 5-formimino-THF.

As mentioned earlier, $C_1$ fragment flow in the leaf can also be provided by exposure to $O_2$-Uptake conditions. $O_2$-Uptake conditions generally include specific stressful environmental conditions such as high light intensity, high temperature, elevated oxygen, and water deprivation, either alone or in any combination. Under conditions such as these, $O_2$-Uptake occurs within the leaf, i.e., the oxygenase activity of Rubisco outcompetes its carboxylase activity. As mentioned earlier, foliar formulations for use under $O_2$-Uptake environments preferably require a $C_1$-acceptor compound. An oxidized substance such as formamidine nitrate that can be reduced by electron carriers from photosynthesis is a preferred exemplary $C_1$-acceptor compound to ensure that metabolism of the $C_1$-fragments by the $C_1$ pathway under $O_2$-Uptake environments is non-toxic and beneficial to the growth of the plant.

$C_1$-acceptor compounds provide $Glu_n$ sources and can be formulated with enhancers or $C_1$-inputs or provided separately. When $C_1$-acceptor compounds are formulated with enhancers or $C_1$-inputs, they may be present as independent substances or they may be part of the same substance as the enhancer or the $C_1$-input substance. For example, a single compound that can act as both $C_1$-acceptor compound and $C_1$-input (salts we denote as $C_1$-acceptor compound·$C_1$-input) would be formamidine·glycolate. In this case, the formamidine portion serves as the polyglutamate source and the glycolate provides the $C_1$-fragment. Similarly, an enhancer such as phthaloylglutamate contains, within its structure, a glutamate as $C_1$-acceptor compound. Other preferred single component enhancer substance formulations in which the $C_1$-acceptor compound is inherent in the molecular make up of the enhancer include, but are not limited to, folinate, pteroyl(Glu)$_n$, phthaloyl(Glu)$_n$, aminobenzoyl(Glu)$_n$, nitrobenzoyl(Glu)$_n$, and the like. $C_1$-acceptor compound substances include compounds such as but not limited to glycine, glutamate, nitrates and formamidines.

As an example of the use of a $C_1$-input, elevated concentrations of $CO_2$ can be applied to plants after application of an enhancer and a $C_1$-acceptor compound. The plant is exposed to the elevated $CO_2$ during daylight hours with continuous exposure to the $C_1$-acceptor compound substance and high light intensity. The plant is moved back to air at night.

Methods of the present invention may comprise two steps, where a formulation of enhancer(s) is applied to the leaves of the plant to initiate enhancement of the $C_1$-THF pool. After passage of a time sufficient to allow for $C_1$-THF accumulation, the plant is exposed to conditions which increase the flow of carbon, such as by foliar application of $C_1$-inputs and $C_1$-acceptor compound or exposure to $O_2$-Uptake conditions and a $C_1$-acceptor compound. Usually, the foliar application of $C_1$-input substance(s) or the exposure to an $O_2$-Uptake condition will be done at least twice following each application of the enhancer substance. Often it will be more than twice over a period from 1 day to 15 days following each enhancer substance application. It will be recognized that even though it is preferable to apply the enhancer substance before the $C_1$-input substance, the order of application may be reversed.

Plant growth promoting compositions according to the present invention may also be formulated for one-step application. Such one-step compositions will comprise an aqueous solution of enhancer(s) and/or $C_1$-input substances in combination with a $C_1$-acceptor compound. The enhancer compounds will be present in amounts sufficient to increase the amount of $C_1$-THF available in foliage when applied to the plant. The $C_1$-acceptor compound will be selected and be present in amounts sufficient to act as a sink for the $C_1$ fragments generated by metabolism through $C_1$-THF (e.g., by increasing $Glu_n$). Preferred enhancers for such a one-step application include, but are not limited to, folinate, nitrobenzoates and phthalates. Preferred $C_1$-inputs for such a one-step application include, but are not limited to, formamidine·glycolate and formamidine·formate. Preferred $C_1$-acceptor compounds for such a one-step application include, but are not limited to, glycine, glutamate, glutamine, and formamidine nitrate.

Compositions according to the present invention include plant growth promoting systems comprised of a first aqueous solution and a second aqueous solution. The first aqueous solution contains an amount of an enhancer substance selected to increase $C_1$-THF when applied to a plant. The second aqueous solution, applied to the plant after application of the first aqueous solution, contains an amount of $C_1$-input+$C_1$-acceptor compound substance selected to increase the flow of carbon in a leaf. Preferred enhancer substances include but are not limited to folinate, pteroic acid, p-nitrobenzoic acid and substituted benzoates, such as terephthalic acid. Preferred $C_1$-inputs include but are not limited to carbon dioxide, glycolate, formamidine·glycolate; formamidine·formate; formiminoamino acids; and other formimino-, methyl-, methenyl-, methylene- and formyl-sources. Preferred $C_1$-acceptor compounds include but are not limited to glutamate, glutamine, glycine and formamidines. Alternatively, the first aqueous solution can contain a $C_1$-acceptor compound substance and the second aqueous solution can contain an enhancer and/or a $C_1$-input.

Another plant growth promoting composition for two-step application according to the present invention is a first aqueous solution comprising an enhancer and a second aqueous solution comprising a $C_1$-acceptor compound. Application of the enhancer is followed by exposure to $O_2$-Uptake conditions and application of the $C_1$-acceptor compound.

In summary, plant growth is promoted by enhancement of $C_1$-THF in the leaf and increased flow of $C_1$ fragments in the $C_1$ pathway by foliar application of $C_1$-acceptor compounds with enhancers, $C_1$-inputs, and/or with exposure to $O_2$-Uptake conditions.

DESCRIPTION OF THE SPECIFIC EMBODIMENTS

Figure 1:
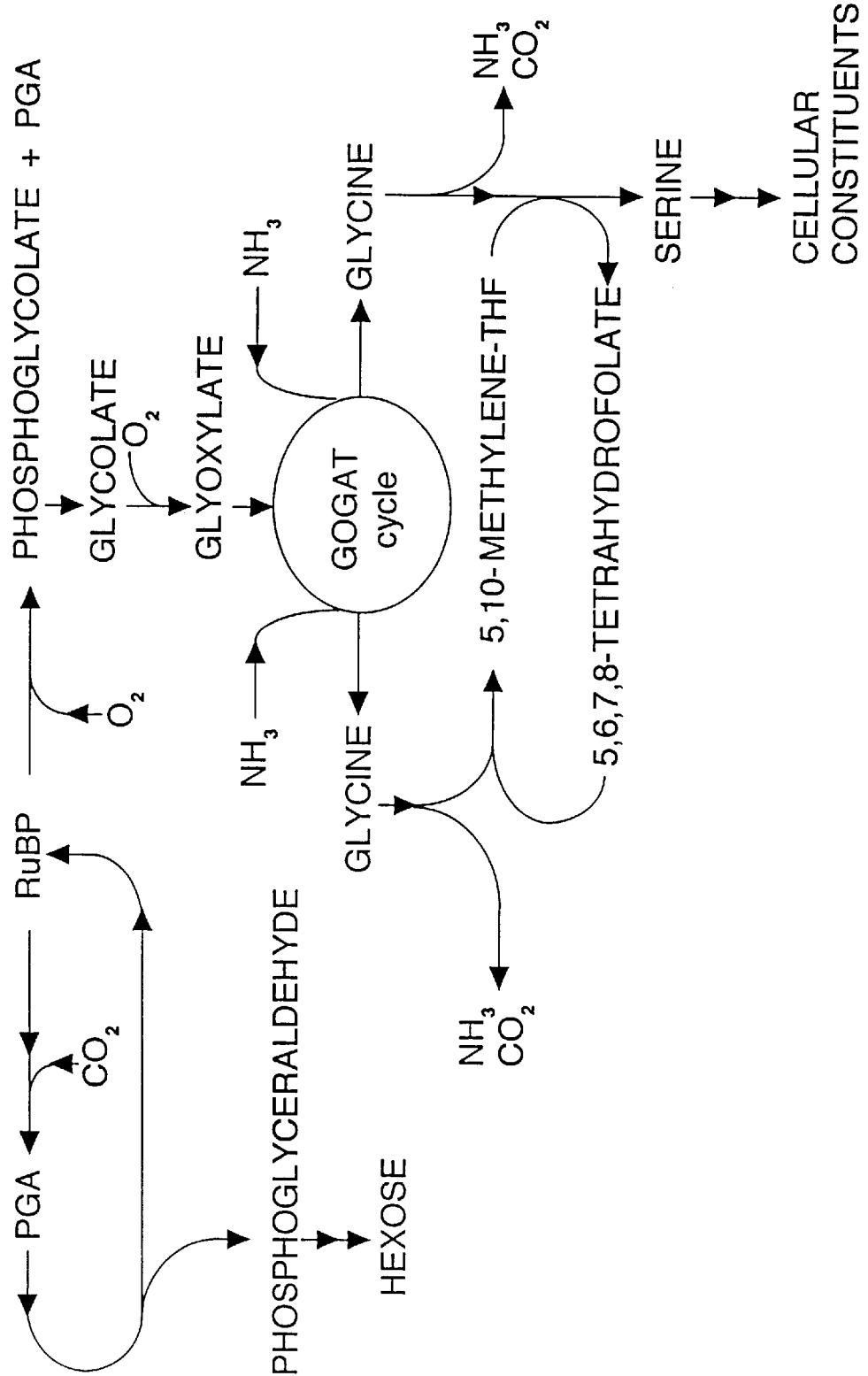
FIG. 1 is a simplified depiction of the $C_3$ photosynthetic pathway in plants.
Figure 2:
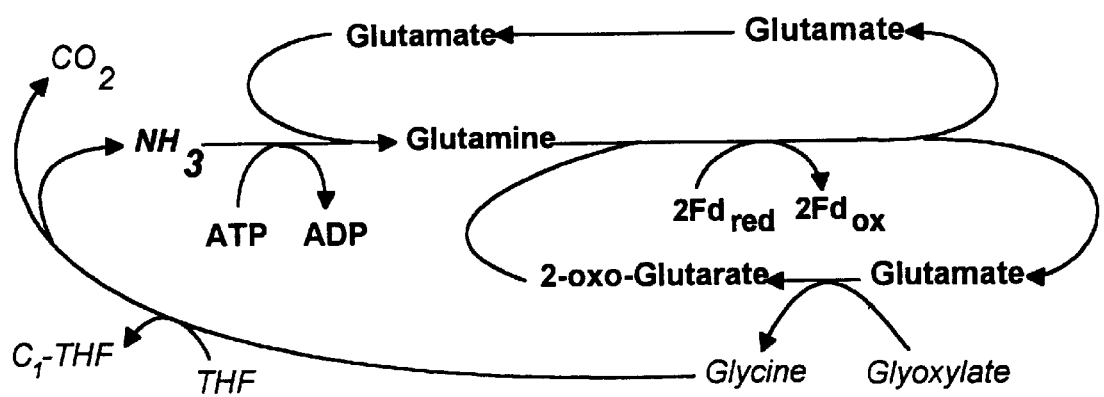
FIG. 2 is an enlarged depiction of the relation between the GOGAT (glutamine: 2-oxoglutarate amino transferase) cycle and oxygen uptake in the $C_3$ photosynthetic pathway in plants.
Figure 3:
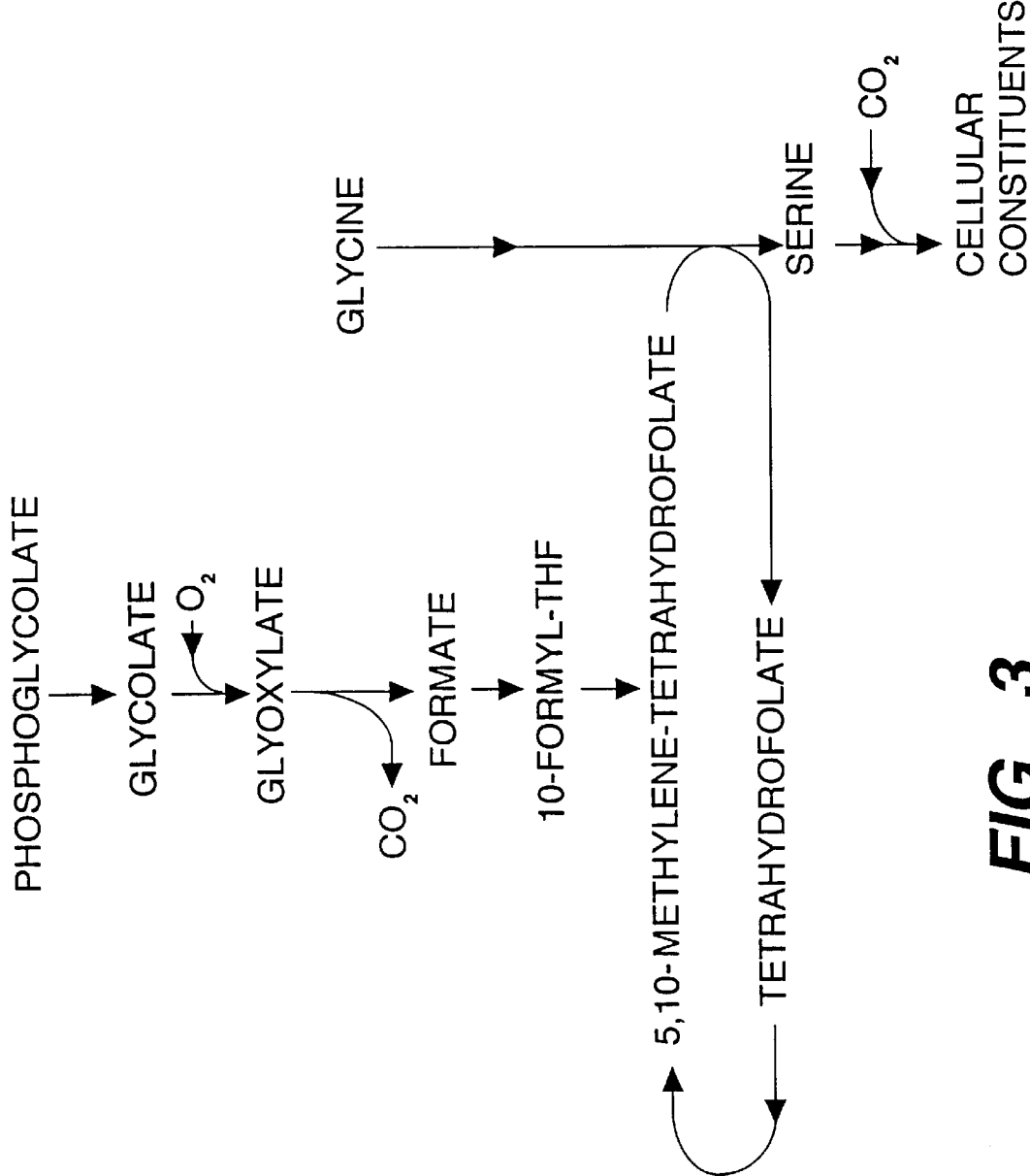
FIG. 3 is a simplified depiction of an alternate pathway for glyoxylate, bypassing the GOGAT cycle.

The present invention provides methods and compositions for promoting the growth of green higher plants, that is, all plants which are actively photosynthetic. The phrase "green higher plants" is intended to include virtually all species with active light-gathering surfaces capable of receiving foliar sprays, particularly higher plants that fix carbon dioxide. "Higher" plants include all plant species having true stems, roots, and leaves, thus excluding lower plants, yeasts and molds. The phrase "$C_3$ plants" refers to all plants capable of fixing carbon via the $C_3$ photosynthetic pathway. Suitable plants which may benefit from $C_1$ pathway carbon fertilization according to the present invention include crop plants, such as cranberry, cotton, tea, onions, garlic, leek, bach ciao, coffee, cassava, mustard, melon, rice, peanut, barley, broccoli, cauliflower, mint, grape, potato, eggplant, zucchini, squash, cucumber, legume, lettuce, kale, sugar beet, radish, kale, tobacco, alfalfa, oat, soy, turnip, parsnip, spinach, parsley, corn, sugar cane, Stevia, sorghum and the like; flowering plants, such as New Guinea Impatiens, geranium, passion fruit, breadfruit, poinsettia, Dusty Miller, mimulus, snapdragon, pansy, fuchsia, lobelia, carnation, impatiens, rose, coleus, chrysanthemum, poppy, gesneriads, bromeliads, bougainvillea, oleander, hibiscus, gardenia, jasmine, camellia, marigold, daisy, stock, vinca, gerbera, carnation, cyclamen, peony, shooting star, bird-of-paradise, forget-me-not, petunia, lily, tulip, crocus, daffodil, lisianthus, borage, and the like; leafy plants, such as philodendron, ficus, and the like; fruit trees, such as apple, plum, peach, cherry, citrus, pistachio, almond, walnut, mango, papaya, guava, cocoa, banana, and the like; forest trees, such as maple, dogwood, oak, yew, fir, pine, redwood, cypress, juniper, elm, birch, palm, mahogany, teak, Christmas trees, and the like; grasses; ferns; and kelps. This list is intended to be exemplary and is not intended to be exclusive.

The methods and compositions of the present invention may be used to promote growth in photosynthetic parts of either juvenile or mature plants. Generally, however, it is desirable that the plants include at least the sprouted cotyledon (i.e., the "seed leaves") or other substantial light-gathering surfaces, including, of course, the true leaves. Improved growth occurs as a result of enhancement of $C_1$-THF as in FIG. 6 or via the $C_1$ pathway of FIGS. 4 and 5. High foliar content of $C_1$-THF maintains high rates of carbon fixation even under detrimental conditions and plant growth is improved. The aqueous solution of the $C_1$-THF enhancer substance will be applied to the leaves of the plant, usually as a foliar spray, but also including dipping, brushing, wicking, misting, and the like of liquids, foams, gels and other formulations. Foliar sprays will comprise atomized or other dispersed droplets of the aqueous solution which are directed at the plant leaves in such a way as to substantially wet the surface of the leaf with the minimum amount of the aqueous solution being lost on the soil. It will be desirable to minimize the amount of aqueous solution which is lost in the soil, with typically at least 75% of the aqueous solution being directed at the leaves, preferably at least 90% by weight, and more preferably substantially all of the solution being directed at the leaves. Such foliar sprays can be applied to the leaves of the plant using commercially available spray systems, such as those intended for the application of foliar fertilizers, pesticides, and the like, and available from commercial vendors such as FMC Corporation, John Deere, Valmont and Spraying Systems (TeeJet™).

Figure 4:
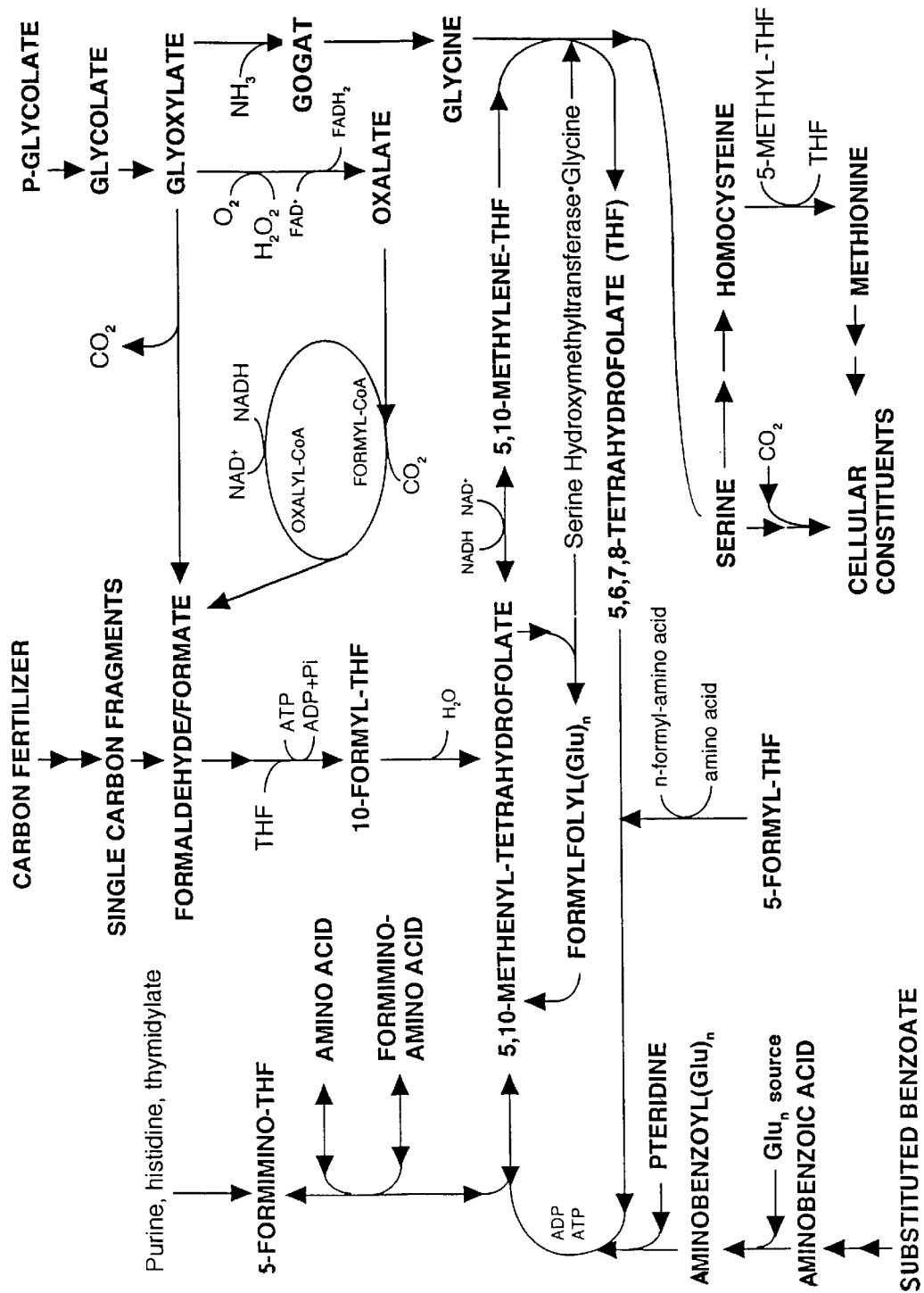
FIG. 4 is a detailed depiction of the $C_1$ pathway, further illustrating paths for enhancing $C_1$-THF and the flow of $C_1$ fragments.
Figure 5:
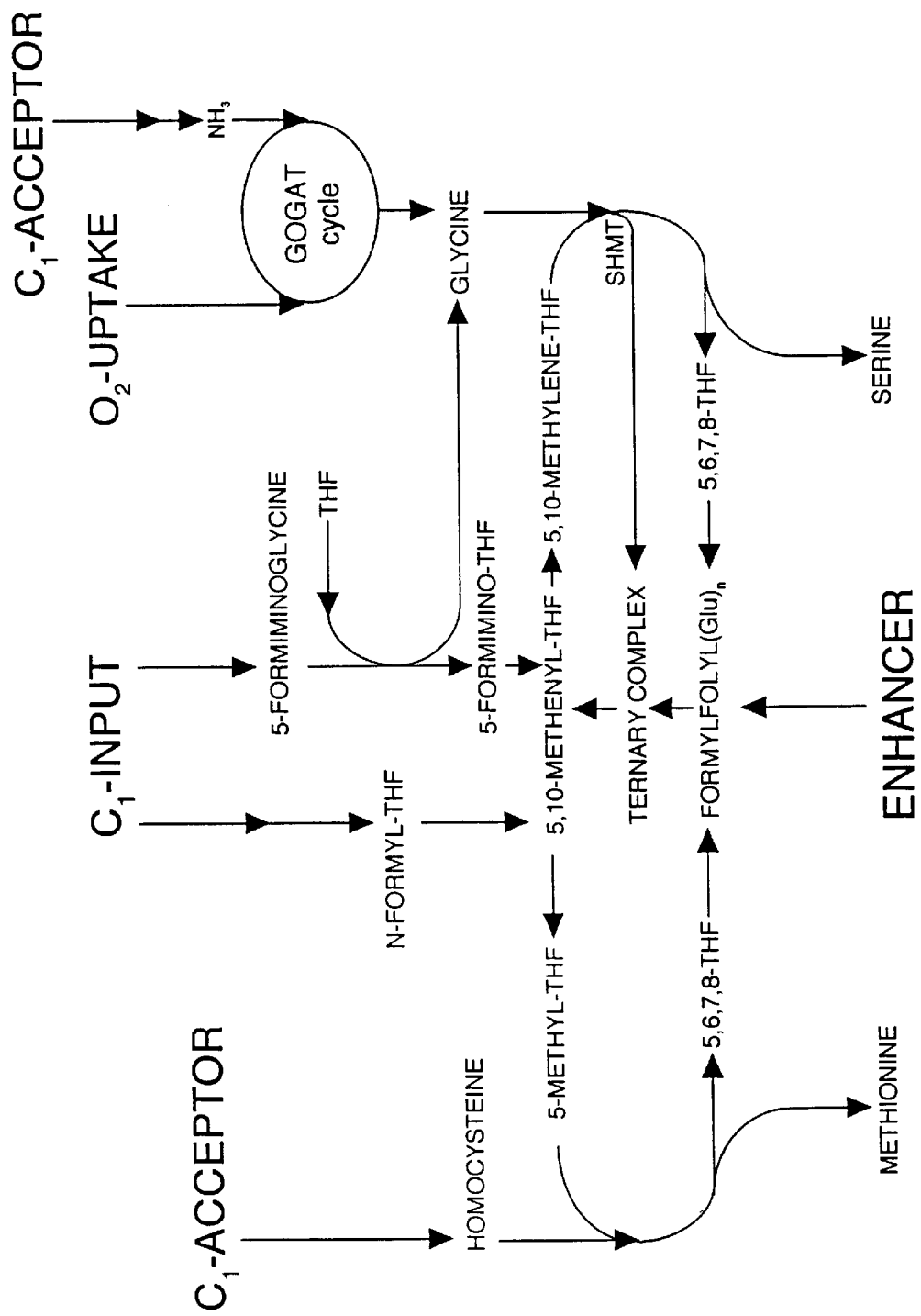
FIG. 5 is a simplified depiction of a $C_1$ pathway, further illustrating paths for enhancers, $C_1$-inputs, $C_1$-acceptor compounds and $O_2$-Uptake.

Several hours before and/or for up to two weeks after application of a $C_1$-THF enhancing substance, the plants will be exposed to conditions which result in an increased activity for production of carbon flow according to the $C_1$ pathway of FIGS. 4 and 5. Conditions include the foliar application of enhancers, $C_1$-inputs, and $C_1$-acceptor compounds and exposure to $O_2$-Uptake conditions. Suitable light and temperature conditions may be achieved by prolonged exposure of the plant to direct sunlight or other suitable high light intensity illumination sources while maintaining optimal to hot temperatures, usually above 20° to 35° C. The plants should remain exposed to the sunlight or high intensity illumination for a period of time sufficient to allow for incorporation of treatments. Usually, the plants should remain exposed to sunlight or other illumination during daylight photoperiods for at least two hours before and for two weeks following fertilizer application. Sufficient nutrients must also be supplied to support healthy growth.

To be sure that there is sufficient $Glu_n$ for carbon fixation, a $C_1$-acceptor compound source is supplied with application of enhancer or $C_1$-input. Enhancer compounds include those which increase $C_1$-THF. Preferred contributors to $C_1$-THF include its fragments such as folinate, pteridines, and substituted benzoates. $C_1$-input substances include those which increase the flow of $C_1$ fragments. Preferred $C_1$-input substances include organic compounds such as formamidine·glycolate and formamidine·formate that yield $C_1$ fragments from $C_1$-acceptor compound·$C_1$-input salts. Preferred $C_1$-acceptor compounds include those such as formamidine nitrate, glycine and glutamate which add to the $Glu_n$ chain. Activator compounds are those in which enhancers will dissolve prior to mixture with an aqueous solution. Preferred Activators also benefit plant growth by contributing nutrients and include methanol, potassium carbonate, potassium hydroxide, calcium hydroxide and acetic acid.

Plant illumination, either sunlight or artificial, should have an intensity and duration sufficient to enhance photorespiration. A minimum suitable illumination intensity is 100 $\mu$mol photosynthetically active quanta (400–700 nm) $m^{-2}$ $s^{-1}$, with direct sunlight normally providing much higher illumination. Leaf temperature should be sufficiently high for optimal growth or hotter, usually above 25° to 35° C. It is preferable that the plant be exposed to at least two and preferably twelve hours of intense illumination following application of formulations.

Elevated carbon dioxide levels will be above normal atmospheric levels, i.e., above about 0.03%, typically being above about 1%, and preferably being above about 10%. Such elevated carbon dioxide levels may be provided in controlled high light intensity environments, such as greenhouses, treatment chambers, protective crop and bedding covers, phytotrons, and other controlled-environment sealed enclosures for plant culture, and the like. Plants are initially treated with an enhancer to stimulate the rate of carbon dioxide fixation. Enhancement of the $Glu_n$ portion of $C_1$-THF by application of a $C_1$-acceptor compound according to the present invention is necessary with exposure of plants to elevated carbon dioxide levels which, in the absence of such, would be toxic to many or all treated plants.

Figure 6:
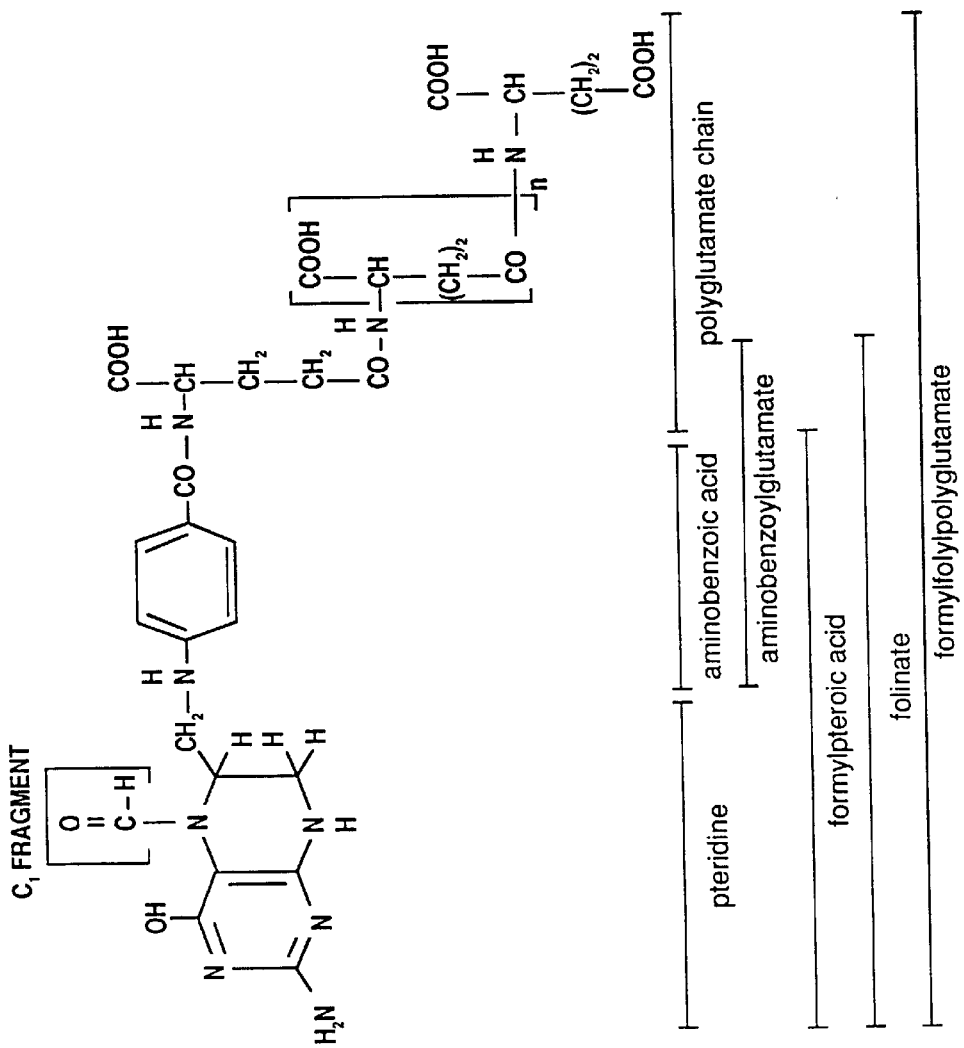
FIG. 6 is a structure of $C_1$-THF with bars corresponding to the various components that can be applied to foliage for enhancement. Attachment of the single carbon fragment at the 5-position of the pteridine structure is shown with regard to availability of the 10- and 5,10-positions, also.

Enhancer, $C_1$-input and $C_1$-acceptor compound substances suitable for use in the methods and compositions of the present invention may be selected with reference to FIGS. 2, 3, 4, and 5 which are depictions of the $C_1$ pathway and FIG. 6 which depicts a representative $C_1$-THF molecule. Enhancer, $C_1$-input and $C_1$-acceptor compound formulations may be applied to plants in sequence or in combination for improved plant growth. For consistency of results and to prevent toxicity, formulations generally include a $C_1$-acceptor compound substance.

Suitable enhancer substances include those compounds which are whole molecules, fragments or precursors of $C_1$-THF in the pathway, as well as all salts, hydrates, aldehydes, esters, amines, and other biologically or chemically equivalent compounds and substances which can be metabolized in the leaf to contribute a component to $C_1$-THF. Preferred enhancer substances include $C_1$-THF compounds, pteridine compounds, and substituted benzoate compounds.

Suitable $C_1$-THF compounds include folinates and compounds which may be converted to N-formyltetrahydropteroyl$(Glu)_n$ when applied to the treated plant. Exemplary $C_1$-THF compounds include folinic acid; anhydroleucovorin; 5-formyltetrahydropteroyl$(Glu)_n$ (depicted in FIG. 5); 10-formyltetrahydropteroyl$(Glu)_n$; 10-formyl-THF; 5-methyl-THF; 5,10-methenyl-THF; 5,10-methylene-THF; 5,6,7,8-THF; 5-formimino-THF; and ethoxylates, salts and hydrates thereof. Such $C_1$-THF compounds will be applied to the plant as an aqueous solution having a concentration in the range from about 0.0001% by weight to 0.5% by weight, preferably to about 0.1% by weight, more preferably about 0.005%.

As a class, pteridines are expected to promote plant growth. These include, but are not limited to neopterin, biopterin, leucopterin and the like. Suitable pteridine compounds contribute to the structure of $C_1$-THF and are represented by the formula below, wherein:

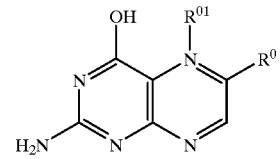

$R^{01}$ is hydrogen or is a hydrocarbyl group capable of being metabolized to a one carbon substituent having the oxidation state of a methyl, hydroxymethyl, formyl or formic acid residue; and $R^0$ is independently selected from the group consisting of: methylene-aminobenzoate, optionally substituted on the benzoate ring; methylene-aminobenzoyl$(Glu)_n$, wherein n is an integer from 0 to 10, optionally substituted on the benzoyl ring; its corresponding dihydro- and tetrahydro-reduction products at positions 5, 6, 7, and/or 8 of the pteridine rings; and salts, hydrates and surfactant-linked derivatives thereof.

For the purposes of this invention the term "hydrocarbyl" shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "optionally substituted hydrocarbyl" refers to a hydrocarbyl group which can optionally be mono-, di-, or tri-substituted, independently, with hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl.

The term "lower" as used herein in connection with organic radicals or compounds respectively defines such with up to and including 6, preferably up to and including 4 and more preferably one or two carbon atoms. Such groups and radicals may be straight chain or branched.

The term "surfactant" refers to surface-active agents, i.e., which modify the nature of surfaces, often by reducing the surface tension of water. They act as wetting agents, dispersants or penetrants. Typical classes include cationic, anionic (e.g., alkylsulfates), nonionic (e.g., polyethylene oxides) and ampholytic. Soaps, alcohols and fatty acids are other examples.

The term "surfactant-linked derivative" refers to a derivative of the parent compound, the derivative having a surfactant covalently attached to the parent compound. A representative example of a parent compound and a surfactant-linked derivative thereof is p-aminobenzoic acid and the corresponding polyethoxylated p-aminobenzoic acid (Uvinul® P-25).

Suitable non-limiting examples of $R^{01}$ include lower-alkyl, alkyl, hydroxymethyl, hydroxyalkyl, 1-hydroxyalkyl, hydroxylower-alkyl, 1-hydroxylower-alkyl, alkoxyalkyl, 1-alkoxyalkyl, alkoxylower-alkyl, 1-alkoxylower-alkyl, haloalkyl, 1-haloalkyl, 1-halolower-alkyl, aminoalkyl, 1-aminoalkyl, 1-aminolower-alkyl, thioalkyl, 1-thioalkyl and 1-thiolower-alkyl.

Exemplary pteridine compounds are pterin; pteroic acid; pteroyl(Glu)$_n$ such as folic acid, pteropterin and pteroylhexaglutamylglutamic acid (PHGA); dihydrofolate; Rhizopterin; xanthopterin, isoxanthopterin, leucopterin; and ethoxylates, salts and hydrates thereof. Such pteridine compounds will be applied to the plant as an aqueous solution in a concentration in the range of about 0.0001% to 0.5% by weight, preferably in the range of about 0.0001% to about 0.1%.

Suitable substituted benzoate compounds contribute to the structure of $C_1$-THF and are represented by the formula below, wherein:

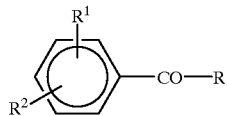

R is H, hydrocarbyl, halogen; —OH; —SH, NH$_2$, N-linked amino acid, N-linked polypeptide, —OR$^3$, —SR$^3$, NHR$^3$, wherein R$^3$ is selected from the group consisting of optionally substituted hydrocarbyl, alkyl, acyl, amino acids or polypeptide chains, —NR$^4$R$^5$ wherein R$^4$ and R$^5$ which may be the same or different and are independently selected from the group consisting of H, optionally substituted hydrocarbyl, alkyl, aryl, acyl, C-terminal linked amino acids, C-terminal linked polypeptide chains, or R$^4$ and R$^5$ together with the nitrogen atoms to which they are linked form a heterocyclic ring;

R$^1$ and R$^2$ are independently selected from the group consisting of: optionally substituted hydrocarbyl groups, alkyl, aryl, acyl, aroyl, halo, cyano, thio, hydroxy, alkoxy, aryloxy, amino, alkylamino, aminoalkyl, arylamino, aminoaryl, acylamino, ureido, alkylureido, arylureido, hydrazino, hydroxamino, alkoxycarbonylamino, aryloxycarbonylamino, nitro, nitroso, carboxy, alkoxycarbonyl, aryloxycarbonyl, aminocarbonyl, carboxamido, monoalkylaminocarbonyl, dialkylaminocarbonyl, formyl, sulfo, sulfamoyl, sulfoamino, alkylsulfonyl, arylsulfonyl, sulfeno, sulfino, alkylsulfino, arylsulfino; and salts hydrates and surfactant-linked derivatives thereof, in an aqueous solution at a concentration in the range from 0.0001% by weight to 0.5% by weight.

Preferably, R$_1$ and $^2$ will be at the 2, 3, or 4 position of the benzoate ring. Cationic salts of the benzoates include cations selected from the group consisting of cations of alkali metals, alkaline earth metals, ammonium, organic ammonium (amine), quaternary ammonium, and mixtures of such salts.

Among the suitable compounds are aminobenzoic acids, such as m-aminobenzoic acid and p-aminobenzoic acid, and derivatives such as N-benzoyl amino acids, N-acyl-aminobenzoic acids, aliphatic aminobenzoate esters, aliphatic N-acyl-aminobenzoate esters, N-acyl-N'-aminobenzoyl-amino acids, N-formylaminobenzoic acids, 2-chloro-4-aminobenzoic acid, and ethoxylates such as Uvinul® P-25; nitrobenzoic acids and derivatives such as m-nitrobenzoic acid, p-nitrobenzoic acid, nitrobenzoyl amino acids, polyethyleneglycol nitrobenzoate, 4-chloro-2-nitrobenzoic acid, 2-chloro-4-nitrobenzoic acid; phthalates, such as, terephthalic acids, phthalic acids, isophthalic acids, phthalic anhydrides, phthaloyl amino acids, and phthalaldehydic acids; formylbenzoic acids; and esters, amides, hydrates and salts thereof. Such substituted benzoates that contribute to the structure of $C_1$-THF will be applied to the plant as an aqueous solution in a concentration in the range from about 0.0001% by weight to 1% by weight, preferably about 0.0001% to 0.5%.

In the process of formulating some enhancer compositions, the substance must first be activated by completely dissolving it in a compatible Activator solution prior to mixture into an aqueous medium. Suitable Activators dissolve with enhancer substances in water and include organic acids, particularly hydrocarbyl acids and aliphatic alkyl acids such as, for example, formic acid, acetic acid, propionic acid and the like. Other Activators include alkali and alkaline earth hydroxides (KOH, NaOH, ammonium hydroxide, Ca(OH)$_2$ and the like); alcohols such as methanol, isopropanol, and ethanol; alkali and alkaline earth carbonates and organic bases such as pyridine, diethylamine; surfactants such as, but not limited to phthalic glycerol alkyd resin (e.g. Latron B-1956™; and penetrants such as organic solvents, particularly dipolar aprotic solvents such as DMSO. Preferred Activators which are also $C_1$-inputs include methanol, trimethylorthoformate, hexamethylenetetramine and DMSO. Penetrants are typically organic solvent-based carriers which enable the applied substance to penetrate into the plant leaf.

The sustained flow of $C_1$-carbon required for rapid growth is preferably accomplished by application of $C_1$-input with $C_1$-acceptor compound to the plant being treated. These $C_1$-input with $C_1$-acceptor compound compositions can be applied as distinctly separate formulations or in combination with enhancers. $C_1$-inputs with $C_1$-acceptor compounds are preferably applied separately after enhancer substances, usually at least about 6 hours after enhancer substances had been applied, and preferably at least one day to one week after the enhancer substance had been applied. Often, the $C_1$-inputs with $C_1$-acceptor compounds will be applied at least twice between successive applications of an enhancer substance, frequently being applied from 2 to 10 times between such successive applications. It would be possible in some cases to apply the $C_1$-inputs with $C_1$-acceptor compounds continuously between successive applications of another enhancer substance. For example, the aqueous solution containing an enhancer substance such as folinate may be applied periodically with successive applications being spaced apart by a period in the range from 7 days to 20 days, with aqueous solutions comprising the $C_1$-input such as formate with a $C_1$-acceptor compound such as glutamine being applied from 1 time to 50 times between such successive applications.

Suitable $C_1$-input compounds that pass $C_1$ fragments include, but are not limited to, formamidine carboxylate salts selected from the group consisting of formamidine glycolate, formamidine acetate and formamidine formate; a formimino amino acid selected from the group consisting of formiminoglycine, formiminoglutamate, formiminoalanine, and formiminoaspartate; a carboxylic acid selected from the group consisting of glycolate, oxalate and formate; an aldehyde selected from the group consisting of formaldehyde and acetaldehyde; a trialkyl orthoester selected from the group consisting of trimethylorthoformate, triethylorthoformate; an N-formylated organic compound selected from the group consisting of diformylhydrazine, formamide, methyl formamide and dimethyl formamide; an acetamide selected from the group consisting of acetamide, methyl acetamide and dimethyl acetamide; carbon dioxide; 1,3,5-triazin-2-one, trimethylamine or hexamethylenetetramine; and salts and hydrates thereof, and other sources of $C_1$ fragments including salts, esters, amines, alcohols, aromatics, aldehydes, carbamates, and the like. The formamidine carboxylates and formimino amino acids exemplified above can act simultaneously as $C_1$-acceptors, since the formamidine and formimino portions can provide sources of $Glu_n$.

Suitable $C_1$-acceptor compounds act as $C_1$ sinks and/or enhance $Glu_n$ as a consequence of $C_1$-THF metabolism. Formamidines, such as, formamidine nitrate, are exemplary $C_1$-acceptor compounds. Other suitable $C_1$-acceptor compounds include, but are not limited to, glycine, glutamine, glutamate, serine, sarcosine, homocysteine, cystathionine, methionine, hexamethylenetetramines, and formamide. Suitable $C_1$-acceptor compounds are also available as conventional nitrogen fertilizers. They include nitrates, ureas, and the like. Nitrate and urea $C_1$-acceptor compounds are utilized differently from conventional fertilizers in the present invention because they are used in combination with enhancers and $C_1$-inputs to enhance carbon fixation. They directly target increases of the polyglutamate component of $C_1$-THF in the leaf. This has a safening effect that eliminates toxicity of $C_1$-inputs. Thereby, application of high concentrations of $C_1$-inputs results in carbon-based growth rather than retarding or killing the plant. The more closely the $C_1$-acceptor compound resembles $Glu_n$, the lower the energy requirement for metabolism; therefore, the simpler compounds of conventional fertilizers generally do not contribute to $C_1$-THF as efficiently as do the preferred $C_1$-acceptor compounds. The $C_1$-acceptor compound may come as an inherent part of the enhancer and $C_1$-input molecules to more fully enhance $C_1$-THF rather than being utilized strictly for nitrogen. Suitable $C_1$-acceptor compounds may also be linked to surfactants to enhance penetration into the leaf, such as, for example, with PEG glutamate or with Hamposyl™ C.

Particularly preferred formulations are p-NBA and urea dissolved in methanol and a surfactant such as Tween® 80. Another preferred formulation comprises phthalic anhydride and hexamethylenetetramine dissolved in methanol and Tween® 80. Other compositions used in this invention are mixtures for promoting growth of a plant comprising an aqueous solution or a nonaqueous material which when combined with an aqueous carrier contains an enhancer such as p-nitrobenzoic acid or folinic acid; a formamidine salt of a carboxylic acid (e.g., formamidine formate or formamidine glycolate) and agronomically suitable additives. Compositions also include mixtures of polyethoxylated p-nitrobenzoic acid, (e.g., $HOCH_2CH_2$—$(CH_2$—$CH_2$—$O$—$)_n$-p-nitrobenzoic acid ($PEG_n$-PNBA), n=an integer from 18 to 30) and agronomically suitable additives.

Compositions of $C_1$-input with $C_1$-acceptor compound will typically be applied at a concentration ranging from about 0.001% by weight to 5% by weight. Preferred $C_1$-input with $C_1$-acceptor compound formulations include trimethylorthoformate with formamidine nitrate applied as an aqueous solution at a concentration in the range of 0.01% by weight to 1% by weight; formate and potassium glutamate applied as an aqueous solution at a concentration in the range from 0.001% by weight to 5% by weight; and glycolate and formamidine nitrate applied as an aqueous solution with glycolate at a concentration in the range from 0.01% by weight to 0.5% by weight and formamidine nitrate in the range from 0.001% to 1% by weight. Ornamentals and other tender nursery plants meant for indoor horticulture will frequently require lower concentrations and perhaps more frequent application than outdoor agricultural crops. The preferred $C_1$-input:$C_1$-acceptor compound ratio will be in the broad range from 1,000:1 to 1:100 to a narrow range of 5:1 to 1:1.

While the compositions of the present invention may consist essentially of the aqueous solutions of $C_1$-acceptor compound substances with enhancers and $C_1$-inputs, they will usually contain other ingredients and components which improve performance in various ways. For example, compositions will usually contain a surfactant present in an amount sufficient to promote leaf wetting and penetration of the active substances, and optionally other components. Suitable surfactants include anionic, cationic, nonionic, and zwitterionic detergents, such as ethoxylated alkylamines, quaternary amines, LED3A™, Teepol™, Tween®, Triton®, Latron™, Dawn™ dish detergent, and the like. Alternatively, or additionally, penetrants, such as, dimethylsulfoxide (DMSO), sodium dodecylsulfate (SDS), formamides, and lower aliphatic alcohols, may be used. Ethoxylation of an active component or otherwise chemically modifying the active components by incorporating a penetrant substance is preferred because, as exemplified by Uvinul® P-25, formulation without additional surfactant is achieved.

In addition to the above enhancers, $C_1$-inputs and $C_1$-acceptor compounds of the present invention, formulations will often include one or more conventional fertilizer constituents such as nitrogen, phosphorus, potassium, and the like. Compositions may further comprise secondary nutrients, such as sources of sulfur, calcium, and magnesium, as well as micronutrients, such as chelated iron, boron, cobalt, copper, manganese, molybdenum, zinc, nickel and the like. Incorporation of such plant nutrients into foliar fertilizer formulations is well described in the patent and technical literature. Other conventional fertilizer constituents which may be added to the compositions of the present invention include pesticides, fungicides, antibiotics, plant growth regulators, and the like.

Compositions according to the present invention may be tailored for specific uses, including water use efficiency; enhanced performance under environmental stress; aftermarket caretaking; floral or fruit optimization, and in all areas of agriculture in which heightened carbon fixation is beneficial. Compositions may also be formulated at very low concentrations for liquid suspension culture media.

FIRST EXEMPLARY TWO-PART COMPOSITION

| Component | Concentration Broad Range | Narrow Range |
|---|---|---|
| ENHANCER IN ACTIVATOR WITH $C_1$-ACCEPTOR COMPOUND | | |
| p-Nitrobenzoic acid | 1–100 ppm | 5–20 ppm |
| Activator (Methanol) | 0.1% to 99% | 1% to 75% |
| Urea | 0.01% to 1% | 0.1% to 0.4% |
| Surfactant (Triton ® X-100) | 0.01% to 0.5% | 0.03% to 0.1% |
| $C_1$-ACCEPTOR COMPOUND · $C_1$-INPUT SOLUTION | | |
| Formiminoglycine | 0.001% to 1% | 0.05% to 0.3% |
| Surfactant (Triton ® CF10) | 0.01% to 0.5% | 0.1% to 0.2% |

SECONDARY EXEMPLARY TWO-PART COMPOSITION

| Component | Concentration Broad Range | Narrow Range |
|---|---|---|
| ENHANCER SOLUTION | | |
| Calcium folinate | 1 ppm to 500 ppm | 5 ppm to 50 ppm |
| Surfactant (Tween ® 80) | 0.01% to 0.5% | 0.05% to 0.1% |
| DMSO | 0.5% to 3% | 0.8% to 1% |
| Glycine | 0.01% to 1% | 0.1% to 0.3% |
| $C_1$-ACCEPTOR COMPOUND · $C_1$-INPUT SOLUTION | | |
| Formamidine · glycolate | 0.01% to 5% | 0.1% to 1% |
| Surfactant (TWEEN ® 80) | 0.01% to 0.5% | 0.05% to 0.1% |

THIRD EXEMPLARY TWO-PART COMPOSITION

| Component | Concentration Broad Range | Narrow Range |
|---|---|---|
| ENHANCER IN ACTIVATOR WITH $C_1$-ACCEPTOR COMPOUND SOLUTION | | |
| p-Aminobenzoylglutamic acid | 10 ppm to 1000 ppm | 50 ppm to 100 ppm |
| Activator (KOH) | 0.01% to 1% | 0.1% to 0.3% |
| Surfactant (TWEEN ® 80) | 0.1% to 1% | 0.2% to 0.5% |
| FeHEEDTA | 0.1 ppm to 5 ppm | 1 ppm to 3 ppm |
| Potassium glutamate | 0.01% to 1% | 0.1% to 0.5% |
| Phosphate buffer | pH 5 to pH 7 | pH 5.5 to pH 6.5 |
| $C_1$-ACCEPTOR COMPOUND $C_1$-INPUT SOLUTION | | |
| Formamidine · glycolate | 0.01% to 5% | 0.1% to 0.2% |
| Surfactant (TWEEN ® 80) | 0.2% to 1% | 0.2% to 0.5% |

For use on plants subjected to $O_2$-Uptake, one-part compositions may be formulated. The one-part composition is typically composed of low concentrations of substances in combination with a surfactant in a single solution. Exemplary one-part compositions follow.

| Composition | Concentration Broad Range | Narrow Range |
|---|---|---|
| EXEMPLARY ONE-PART COMPOSITION FOR USE ON PLANTS WITH $O_2$-UPTAKE | | |
| Uvinul ® P-25 | 0.01% to 1% | 0.1% to 0.5% |
| Potassium nitrate | 0.01% to 0.3% | 0.1% to 0.2% |
| SECOND EXEMPLARY ONE-PART COMPOSITION FOR USE ON PLANTS WITH $O_2$-UPTAKE | | |
| Formiminoglutamate | 0.01% to 1% | 0.1% to 1% |
| Potassium glycolate | 0.01% to 1% | 0.2% to 3% |
| Calcium nitrate | 0.01% to 1% | 0.1% to 0.3% |
| Surfactant (HAMPOSYL ™ C) | 0.01% to 0.1% | 0.02% to 0.05% |
| THIRD EXEMPLARY ONE-PART COMPOSITION WITH ACTIVATOR FOR USE ON PLANTS WITH OUPTAKE | | |
| Phthalic anhydride | 1 ppm to 100 ppm | 15 ppm to 50 ppm |
| Activator (DMSO) | 0.01% to 3% | 0.5% to 1% |
| Potassium glycolate | 0.001% to 0.3% | 0.1% to 0.2% |
| Formamidine nitrate | 0.01% to 1% | 0.1% to 0.3% |
| Surfactant (HAMPOSYL ™ L95) | 0.05% to 1% | 0.1% to 0.2% |
| FOURTH EXEMPLARY ONE-PART COMPOSITION WITH ACTIVATOR FOR USE ON TURF | | |
| Phthaloylglutamate | 1 ppm to 100 ppm | 15 ppm to 50 ppm |
| Activator (Methanol) | 0.1% to 99% | 3% to 90% |
| Iron EDTA | 0.1 ppm to 3 ppm | 0.5 ppm to 1 ppm |
| Surfactant (Latron B-1956 ™) | 0.01% to 0.5% | 0.02% to 0.1% |

The following examples are offered by way of illustration, not by way of limitation.

Experimental

Materials and Methods

Chemicals (abbreviations) and sources: sodium glutamate, Ajinomoto; formamidine formate (FAF), glycine (Gly), HAMPOSYL™ C, potassium glycolate (GO), potassium phosphate (KOH), and purified water,Hampshire Chemical Corporation; adenosine triphosphate (ATP), m-aminobenzoic acid (MABA),p-aminobenzoic acid (pABA),p-aminobenzoic acid ethyl ester (Benzocaine™), (p-aminobenzoyl)-L-glutamic acid (pABG),p-aminohippuric acid (pAH), anthranilate (oABA), ascorbic acid, ethanol (EtOH), folic acid (Folate), calcium folinate (Folinate), formaldehyde, formamidine acetate (FAM), formic acid, formiminoglycine (FIGly), formiminoglutamate (FIGlu)$_n$,p-formylbenzoic acid (pFBA), methanol (MeOH), methyl-2-anthranilate (MeoABA), nicotinamide adenine dinucleotide phosphate (NADP), terephthalic acid (CBA), N-phthalolyl-L-glutamate (CBG), potassium maleic acid (Malate), potassium chloride (KCl), pteroic acid (Pteroic), 5,6,7,8-tetrahydrofolate (THF), n-[2-hydroxyethyl] piperazine-N'-[ethanesulfonic acid], aprotinin, 2-mercaptoethanol, triethanolamine, ammonium formate, magnesium chloride (MgCl$_2$), Tween® 80 and Triton® X-100, Sigma-; p-nitrobenzoic acid (pNBA), Dupont; dimethylsulfoxide (DMSO), Gaylord; ethoxylated p-aminobenzoic acid (Uvinul® P-25), BASF; $^{14}CO_2$, ICN; 2,4-dinitrobenzoic acid (DNBA), 2-chloro-4-nitrobenzoic acid (CNBA), 4-chloro-2-nitrobenzoic acid (NCBA), 2,4-dichlorobenzoic acid (2C1BA), Aldrich.

Radioisotopic $^{14}CO_2$ was applied to plants to determine the fate of active substances and changes in the path of carbon fixation. Cabbage plants were sprayed with one of the following three solutions: 1) 90 µM folinate, 0.2% glycine, 1% DMSO, and 0.1% Triton® X-100; 2) 40% MeOH, 0.2% glycine, and 0.05% Hamposyl™ C; 3) 0.5 mM pABG, 0.2% glycine, and 0.05% Hamposyl™ C. At 24 h to 48 h, plants were removed from the glass house and placed under a quartz halogen light (type EKE, 21 V, 150 watt) at room temperature and allowed to acclimate to our laboratory conditions for 15–30 min. A leaf that was to be used for experiments was placed in an open chamber that was constantly flushed with pure $O_2$ during the acclimation period. A leaf plug, 3.67 cm$^2$, was then removed, and placed in a hermetically sealed Plexiglass™ leaf chamber containing pure $O_2$ being pumped at a rate of 2–3 L min$^{-1}$. The chamber was illuminated with 1,000 μmol photosynthetically active quanta m$^{-2}$s$^{-1}$ directed through a fiber optic cable connected to a quartz halogen light similar to the one used for preillumination. After 1 min, 5 mL $CO_2$ containing 0.8 μCi Na$^{14}CO_2$ (specific activity of 5 Ci mol$^{-1}$) was injected with a syringe to a final concentration of about 700 ppm $CO_2$. The leaf plugs were allowed to incorporate $^{14}CO_2$ for 15, 60 or 180 s, and then fixation was immediately stopped. In other experiments the leaf plugs were pulsed for 15 s, then chased for 1 min or 3 min. The chase was carried out under ambient air. Fixation was stopped by placing the leaf disc in boiling EtOH containing formic acid. Stable fixed $^{14}CO_2$ containing products were separated by paper chromatography as previously described (R. D. Gates, 0. Hoegh-Guldberg, M. J. McFall-Ngai, K. Y. Bil, and L. Muscatine (1995) "Free amino acids exhibit anthozoan "host factor" activity: They induce the release of photosynthate from symbiotic dinoflagellates in vitro, " *Proc. Natl. Acad. Sci. USA* 92:7430–7434).

Enzymes related to $C_1$-THF were tested for enhancement following treatments. The three enzymes that comprise $C_1$-THF-synthase, 10-formyl-THF-synthetase (EC 6.3.4.3), 5,10-methenyl-THF-cyclohydrolase (EC 3.5.4.9), and 5,10-methylene-THF-dehydrogenase (EC 1.5.1.5) were assayed according to methods of Edwin A. Cossins (University of Alberta, Edmonton, Canada). Leaf tissue was extracted in 25 mM n-[2-hydroxyethyl]piperazine-N'-[ethanesulfonic acid], 0.3 μM aprotinin, 10 mM KCl, and 10 mM 2-mercaptoethanol, adjusted to pH 7.5 with KOH.

10-formyltetrahydrofolate-synthetase catalyzes the reaction, formate+THF+ATP→10-formyl-THF+ADP+Pi. A test tube containing 100 μL 1 M triethanolamine buffer (pH 7.5), 100 μL 1 M ammonium formate (pH 7.5), 100 μL 25 mM $MgCl_2$, 100 μL 2 M KCl, 100 μL 10 mM THF, freshly made 100 μL 20 mM ATP, and 390 μL water was pre-incubated for 2 min at 30° C. A 10 μL aliquot of the extracted sample containing enzyme was added and incubated 15 min at 30° C. The reaction was terminated by adding 2 mL 0.36 N HCl. The 10-formyl-THF formed during the incubation period was converted to 5,10-methenyl-THF by the acid. The absorbency was measured at 350 nm against a water blank and the 5,10-methenyl-THF formed was determined by using an extinction coefficient of 24,900 M$^{-1}$ cm$^{-1}$.

5,10-Methylenetetrahydrofolate-dehydrogenase catalyzes the reaction, 5,10-methylene-THF+NADP$^+$→5,10-methenyl-THF+NADPH+H$^+$. A 0.95 mL solution containing 1 μmole THF, 10 μmoles formaldehyde (fresh), 0.6 μmoles NADP and 25 μmoles n-[2-hydroxyethyl]piperazine-N'-[ethanesulfonic acid] was pre-incubated for 2 min at 30° C. Enzyme in the extraction buffer (50 μL) was then added. After the incubation continued for 15 min at 30° C., 2 mL 1 N HCl was added to stop the reaction. After 15 min at room temperature, the absorbency was measured at 355 nm. A blank containing water was used. The 5,10-methenyl-THF formed was determined using an extinction coefficient of 24,900 M$^{-1}$ cm$^{-1}$.

5,10-Methenyltetrahydrofolate-cyclohydrolase catalyzes the reaction, 5,10-methenyl-THF+$H_2O$→10-formyl-THF. A test tube containing 100 μL 1 M 2-mercaptoethanol, 200 μL 1 M malate buffer (pH=8.0), 50 μL 1.5 mM 5,10-methenyl-THF and 550 μL water was preincubated 3 min at room temperature. A 100 μL aliquot of extraction buffer containing enzyme for hydrolysis of substrate was measured as a change in absorbency at 355 nm for 5 min. The substrate 5,10-methenyl-THF was generated from folinate. We dissolved 7.6 mg folinate in 9.64 mL 0.1 N HCl. We added 0.36 mL 1 M 2-mercaptoethanol and incubated for 24 h at 25° C. in a dessicated vacuum in the dark. The solution was stored dessicated at 4° C. in the dark. Each 50 μL aliquot contained 75 nmoles of 5,10-methenyl-THF.

Protein content of samples was determined by a modified Lowry Procedure, (J. N. Nishio, S. E. Taylor, N. Terry (1985) "Changes in Thylakoid Galactolipids and Proteins during Iron Nutrition-Mediated Chloroplast Development," *Plant Physiol.* 77:705–711).

Gas exchange, enzyme and radioisotope assays were undertaken at the Department of Botany, University of Wyoming, Laramie, Wyo. For gas exchange experiments, soy (*Glycine max* cv Corsoy (variety 9007 and 9008 Pioneer, Johnston, Iowa), sugar beet ((*Beta vulgaris* L) cv NB1×NB4 (United States Agricultural Research Station, Salinas, Calif.) or cv Monohikari (Seedex, Longmont, Colo.)), sunflower (*Helianthus anuus*) and cabbage (*Brassica oleracea* var. Capitata) were soil-cultured in 5" pots containing Metro-Mix™ 350 growing medium (Grace Horticultural Products, W. R. Grace & Co., Cambridge, Mass.) or Peter's™ Professional Potting Soil (Scotts-Sierra Horticultural Products Co., Marysville, Ohio) containing complete nutrient pellets (Sierra 17-6-12 Plus Minors, Grace Sierra, Milpitas, Calif.) in controlled environmental growth chambers (16 h light:8 h dark photoperiod, 400–700 μmol photosynthetically active quanta m$^{-2}$s$^{-1}$, 24–30° C. and 30% RH). Alternatively, plants were cultured in greenhouses with supplemental light provided by 1,000 watt metal halide arc lights (16:8 h photoperiod; 28°:16° C.). Plants were watered daily with measured amounts of reverse osmosis purified water. Photosynthetic $CO_2$ Gas Exchange was determined by taking measures with CIRAS-1 (PP Systems, Bedford, Mass.)or LI-6200 (LI-COR™, Inc., Lincoln, Nebr.) portable gas exchange system.

The quantity of the $C_1$-THF pool was determined in two steps. Culture, treatment, collection and preparation of samples for shipment was undertaken at the University of Wyoming. Microbial assays were undertaken at the University of Alberta. Sugar beets ((*Beta vulgaris* L.) cv Monohikari (Seedex, Longmont, Colo.)) were grown under standard greenhouse conditions described above. Foliage was treated with 14.8 M MeOH, 10 mM FIGly or 0.1 mM folinate dissolved in standard aqueous solutions of 0.05% HAMPOSYL™ C and 0.3% glycine. After treatment with FIGly (20 h) and folinate (20 h), gas exchange was measured to insure that plants were healthy and responsive when the tissues were sampled at that time. Gas exchange was nearly doubled by these treatments and the $C_1$-THF synthases showed approximately 20% stimulation over the controls. The MeOH sample was collected 72 h after treatment when gas exchange measured approximately 50% and enzymes were approximately 20% over the controls. In the preparation of tissue extracts for $C_1$-THF pool quantification, 0.5 g fresh live leaf tissue from different plants was placed in 61 mM ascorbate buffer (pH 6 adjusted by KOH). The samples were then immediately placed in a boiling water bath for 15 min. After cooling, the tissues were homogenized and centrifuged at 18,000 g for 10 min. The supernatant was collected. The pellet was extracted two more times and the supernatants were combined. The samples were sealed, frozen and packed on dry ice for express shipment to the University of Alberta (Department of Biological Sciences, Faculty of Science, Edmonton, Canada). Upon receipt, E. A. Cossins and S. Y. Chan applied the sugar beet leaf extracts to *Lactobacillus rhamnosis* (ATCC 7469) assays based on microbial assay methods of D. W. Horne and D. Paterson (1988) *Clinical Chemistry* 34: 2357–2359; and methods for determination of $C_1$-THF pools in plants including preparation of γ-glutamyl carboxypeptidase were developed by E. A. Cossins (see Cossins 1980 and 1987; Cossins et al. 1993; Besson et al. 1993, infra). Assays determined the content of short-chained pteroyls and total $C_1$-THF pool. The $Glu_n$ value is the difference between the short-chained and total pool values. For each sample, 4 replicate measurements were made.

In an experiment designed to test tolerance to drought stress, three soy plants were treated with 2 $\mu$M folinate with Triton® X-100 surfactant. The plants were watered daily, all pots receiving the same measured amount of water or water plus nutrients to establish a baseline. Subsequently, water was withheld until the soil was extremely dry. The plants were rewatered after extensive prolonged wilt was observed in the controls. The assay relied on death as an endpoint for controls since water stress can be controlled to lethal dose. Treatments that prevented death provided a simple visible determination of remedy. Field tests were undertaken on plants first treated with folinate and followed by post-treatment with glycolate and glycine under conditions of limited and high-rate photorespiration. The formulations included 50 $\mu$M folinate, 40 mM glycolate and/or 40 mM glycine each with Triton® X-100 surfactant sprayed on tomato plants grown identically in movable containers. Four hours following treatment, the plants were moved from direct sunlight to shade or the reverse.

In experiments to measure growth yields, plants were cultured in greenhouses or Percival™ growth chambers at the University of Massachusetts Cranberry Experimental Station, East Wareham, Mass. The plants were grown in 8 to 16 cm diameter pots containing Perlite™ with Vermiculite™ and topsoil. In greenhouses, no special control of physical conditions was attempted, but all comparable treatments were made simultaneously and were subjected to normal greenhouse conditions. Each sample was tested on 4 or more replicate containers of plants. Plants were generally harvested and analyzed in the vegetative stage 6 to 8 days after treatment. Each pot received 3 ml to 5 ml of solution per treatment applied with a small hand-held sprayer constructed of an atomizer head attached to a 5 ml syringe. Individual plants were treated by spraying approximately 0.1 ml/cm$^2$ of solution to leaves. Generally, compounds were optimized by bracketing around the following concentrations: 0.05 mM folinate, 1 mM aminobenzoate, 0.1 mM substituted benzoates, 2 mM formimino-amino acids, 20 mM formates, 30 mM amino acids and 10 M alcohols in aqueous solution. With the exception of Uvinul® P-25, foliar treatments contained 0.5 ml/L of surfactant selected from HAMPOSYL™ C, Tween® 80, or Triton® X-100. Hoagland solution nutrients in water were routinely supplied as needed. Seven to ten days after the last treatment, the plants were removed from pots and the roots were cleaned. Shoot and root lengths and fresh and dry weights were determined. Changes in shoot and root growth were recorded in all cases, but data on roots is given only for radish tests while data on shoot growth is given for other plants. All experiments used 4 replicates and results were subjected to analysis of variance and mean separation by LSD test and showed significance within narrow standard deviations in all cases. The concentrations of compounds were bracketed around optimal concentrations for growth. The plants tested for growth response included radish (cv Cherry Bell), wheat (cv Stoa), rice (cv M-202) and corn (cv Butter Sugar).

All solutions were applied as aqueous foliar sprays. Growth was inhibited in some detergent-treated controls as compared to controls that were not treated with detergent, therefore, depending on the plant type or intent of the experiment, controls were sprayed with water or with the diluent solution minus the active ingredient or controls went without any treatment as a means of comparing against situations that did not decrease growth, enzyme activity or photosynthesis. Based on tests of a gradient of concentrations, 0.05% HAMPOSYL™ C was found to yield 100% growth in investigations undertaken at the Cranberry Experimental Station. Baselines of 100% growth were established for comparisons of growth of controls against each active substance. In order to avoid redundant expression of results, the percentage of change in growth caused by the tested substance is presented from which the control data can be back-calculated. Mixtures of active materials were formulated from a selection of the following control solutions: (A) 0.05% HAMPOSYL™ C, (B) 0.2% glycine+0.05% HAMPOSYL™ C, (C) 200 ppm potassium formate+0.2% glycine+0.05% HAMPOSYL™ C, (D) water, and (E) no foliar treatment. Diseased or aberrant plants were eliminated prior to test. Insects were avoided by weekly treatments with Diazinon™ or other appropriate insecticide in water.

Folic acid and substituted benzoates did not dissolve at sufficiently high concentrations in water to show activity, however, they were sufficiently soluble in MeOH, DMSO, hexamethylenetetramine, trimethylorthoformate, formic acid, acetic acid, pyridine, calcium hydroxide or potassium hydroxide to stimulate responses consistent with enhancement of $C_1$-THF. The enhancers were, thus, activated by dissolving high concentrations in small volumes of one of the above compounds and adjusting to pH 6 to pH 7 prior to formulation in water. Activation in solvents such as DMSO or MeOH allowed convenient effective concentrates to be formulated, for example, 68 mg pNBA+2 gm Triton® CF10+1 gm acylglycine dissolve in 25 ml MeOH; or 100 mg CBA+2 gm Latron B-1956™+0.2 gm formamidine nitrate dissolve in 20 ml DMSO. The concentrates can be stored for later dilution into 4 liters of water for application to foliage.

Results

As shown in Table 1, rate of initial uptake of $^{14}CO_2$ after the 15 second pulse and 1 minute chase in treated plants was higher than in untreated controls. Fixation of $^{14}C$ into the insoluble fraction is greater in treated plants than in controls at 3 minutes.

TABLE 1

PULSE-CHASE SHOWS RAPID $^{14}CO_2$ FIXATION

| Compound | Treatment Concentration | 15 sec $^{14}CO_2$ 60 sec $^{12}CO_2$ | 15 sec $^{14}CO_2$ 180 sec $^{12}CO_2$ |
|---|---|---|---|
| Control | 0 | 4.8 ± 0.2 | 6.6 ± 0.5 |
| pABG | 1 mM | 8.2 ± 0.5 | 3.3 ± 0.2 |
| Folinate | 0.05 mM | 8.5 ± 0.8 | 4.2 ± 0.2 |

TABLE 2

$^{14}CO_2$ FATE: HIGH GLYCINE:SERINE RATIO

| Compound | Treatment Concentration | Serine | Glycine:Serine 3 min |
|---|---|---|---|
| Control | 0 | 13.51 | 0.76 |
| MeOH | 5000 mM | 8.81 | 0.84 |
| pABG | 1 mM | 7.58 | 2.13 |
| Folinate | 0.05 mM | 3.06 | 4.38 |

In Table 3, below, $^{14}CO_2$ light saturated photorespiratory pulse-chase results showed increases in treated plants over controls that were not treated for glycine+serine and 3-phosphoglycerate+phosphoric ethers of sugars at the initial pulse of $^{14}CO_2$. Thereafter, at the 60 second chase, the glycine+serine products decreased when the sugars increased in treated plants as compared to controls.

TABLE 3

$^{14}CO_2$ PULSE-CHASE:RAPID METABOLISM TO SUGAR

| Compound | $^{14}CO_2$ | $^{12}CO_2$ | PGA+PES* | Sugars | Glycine+Serine |
|---|---|---|---|---|---|
| Control | 15 s | | 1.98 | 0.16 | 1.79 |
| | 15 s | 60 s | 1.64 | 1.64 | 3.36 |
| pABG | 15 s | | 5.23 | 0.39 | 1.73 |
| | 15 s | 60 s | 1.74 | 2.94 | 1.27 |
| Folinate | 15 s | | 4.92 | 0.26 | 2.09 |
| | 15 s | 60 s | 1.43 | 3.46 | 1.29 |

*PGA:phosphoglyceric acid. PES: phosphoric ethers of sugars

As shown in Table 4, below, folinate, folate, pABA, pABG, Uvinul®, Benzocaine™, mABA, pNBA, pNBA+glycine, pFBA+glycine, CBA, pAH, FIGly and MeOH activated $C_1$-THF enzymes, but glycine, Hamposyl™ C, FAM and oABA did not. Folinate increased enzyme activity in corn. The addition of glycine to pNBA did not depress the overall stimulation of $C_1$-THF enzymes as compared against similar glycine levels that, alone, depressed enzyme activity. This result is indicative of the synergistic involvement of the metabolism of enhancers with $C_1$-acceptor compounds.

TABLE 4

$C_1$-THF Enzyme Analysis

| Treatment | Species | Concentration | Cyclohydrolase | Synthetase | Dehydrogenase | Sample |
|---|---|---|---|---|---|---|
| | | | Treatment Activity/Control Activity | | | |
| HAMPOSYL ™ C | Sugar beet | 2 mM | 0.93 | 0.7 | 0.61 | 3 |
| HAMPOSYL ™ C | Cabbage | 2 mM | 0.51 | 0.86 | 0.86 | 3 |
| HAMPOSYL ™ C | Soy | 2 mM | 0.96 | 0.78 | 0.98 | 3 |
| Folinate | Sugar beet | 0.1 mM | 2.58 | 2.23 | 2.66 | 2 |
| Folinate | Corn | 0.2 mM | 0.97 | 1.45 | 1.26 | 3 |
| Folate | Cabbage | 0.11 mM | 1.12 | 1.10 | 0.83 | 2 |
| pABA | Sugar beet | 0.5 mM | 4.1 | 1.48 | 2.05 | 2 |
| pABA | Cabbage | 0.5 mM | 1.7 | 1.17 | 1.84 | 2 |
| pABG | Soy | 0.5 mM | 1.87 | 1.43 | 1.26 | 2 |
| Uvinul ® | Sugar beet | 0.5 mM | 1.97 | 1.14 | 1.93 | 6 |
| Benzocaine ™ | Sugar beet | 0.06 mM | 2.5 | 1.82 | 4.03 | 3 |
| Benzocaine ™ | Cabbage | 0.06 mM | 1.1 | 1.07 | 1.16 | 3 |
| mABA | Sugar beet | 5 mM | 1.73 | 1.24 | 2.04 | 6 |
| oABA | Sugar beet | 0.5 mM | 0.61 | 0.68 | 0.51 | 3 |
| oABA | Cabbage | 0.5 mM | 0.69 | 0.76 | 0.41 | 3 |
| pNBA | Sugar beet | 1 mM | 1.37 | 1.49 | 1.56 | 6 |
| pNBA | Cabbage | 1 mM | 1.24 | 0.95 | 1.09 | 5 |
| pNBA + Glycine | Cabbage | 1 mM + 30 mM | 1.38 | 1.05 | 1.21 | 3 |
| CBA | Sugar beet | 0.15 mM | 1.58 | 1.47 | 1.52 | 3 |
| Glycine | Cabbage | 71 mM | 0.93 | 0.69 | 0.97 | 2 |
| FAM | Cabbage | 30 mM | 0.43 | 0.25 | 0.77 | 3 |
| FAM | Sugar beet | 30 mM | 0.65 | 0.77 | 0.7 | 6 |
| pAH | Sugar beet | 0.5 mM | 0.87 | 0.85 | 1.19 | 3 |
| pAH | Cabbage | 0.5 mM | 1.91 | 0.5 | 0.93 | 2 |
| FIGly | Sugar beet | 2 mM | 2.86 | 1.46 | 2.09 | 7 |
| FIGly | Sugar beet | 10 mM | 1.27 | 1.1 | 1.4 | 10 |
| pFBA + Glycine | Cabbage | 0.5 mM | 1.54 | 1.50 | 1.56 | 3 |
| MeOH | Sugar beet | 14,800 mM | 1.22 | 1.43 | 1.4 | 6 |

As shown in Table 5, below, gas exchange was enhanced significantly in soy, sunflower, cabbage, kale and sugar beet by foliar treatments with folate, folinate, pABA, pNBA, pFBA, Uvinul® P-25, FIGly, FAM, FAM with GO, Benzocaine™ and MeOH. Gas exchange was significantly higher after Uvinul® P-25 treatments as compared to pABA treatments. To a small extent, pAH stimulated gas exchange in soy. Neither oABA nor MeoABA showed increases in gas exchange.

Figure 8:
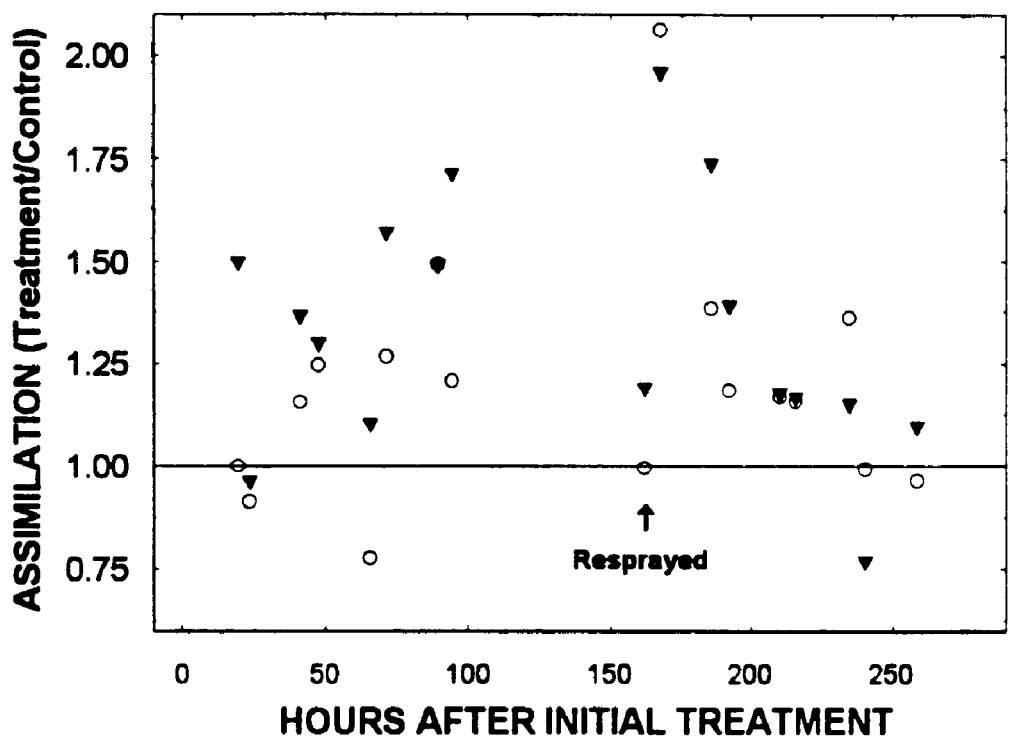
FIG. 8 is a graphic depiction of results of experimentation showing the long-term effects of Uvinul® P-25 or formiminoglycine on $CO_2$ gas exchange. Leaves of sugar beets were sprayed with 0.5 mM Uvinul® P-25, 13 mM glycine and 0.05% Hamposyl™ C (o); or 2 mM formiminoglycine, 13 mM glycine and 0.05% Hamposyl™ C(▽). Each point is the mean of 3 to 6 measurements of foliar $CO_2$ gas exchange.

FIG. 8 shows that 0.5 mM Uvinul® or 2 mM FIGly applications to sugar beet increased $CO_2$ gas exchange for ten days following treatments.

Figure 9:
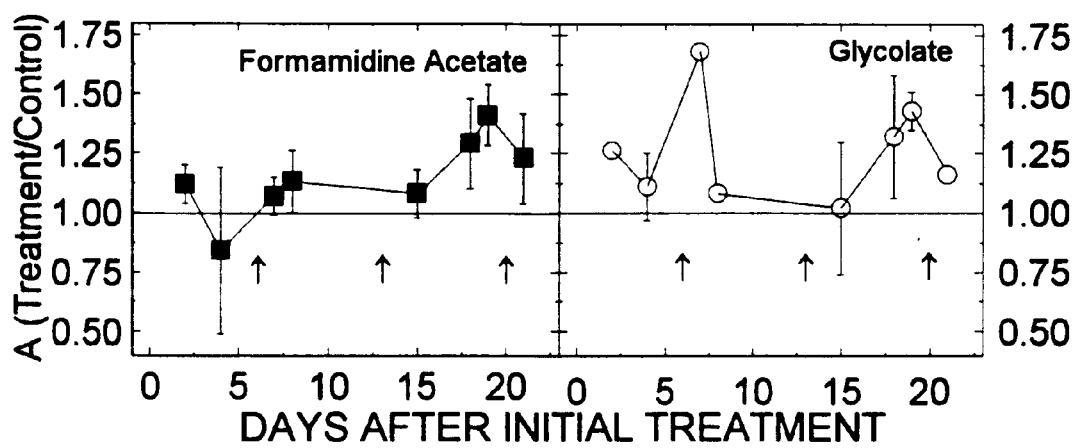
FIG. 9 is a graphic depiction of results of experimentation showing the long-term effects of formamidine acetate or potassium glycolate on $CO_2$ Assimilation (A). Soy foliage was sprayed with 30 mM formamidine acetate (FAM) plus 0.05% Hamposyl™ C (left frame) or 30 mM potassium glycolate plus 0.05% Hamposyl™ C (right frame). Arrows indicate when plants were treated. Each point is the mean of 3 separate measurements±SD. No SD shown is less than symbol size.

FIG. 9 shows that 3 foliar sprays of 30 mM FAM or 30 mM GO formulations increased gas exchange over controls for approximately a week between treatments.

Figure 10:
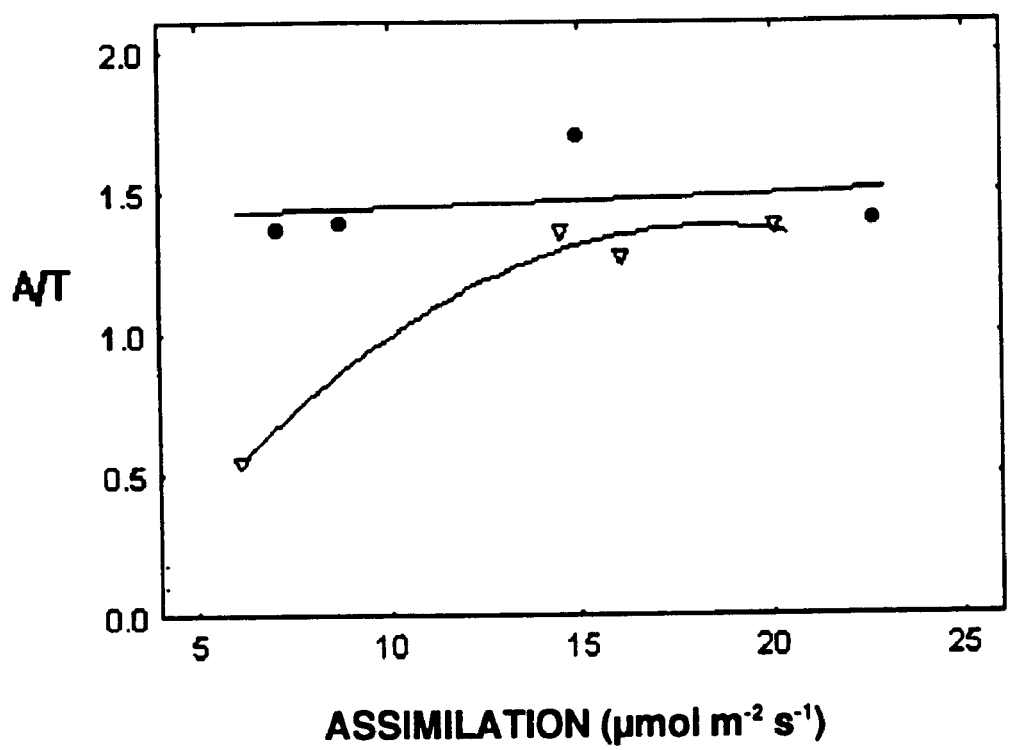
FIG. 10 is a graphic depiction of results of experimentation showing the long-term effects of formamidine acetate on the Assimilation/Transpiration (A/T) ratio. Cabbages were sprayed with 30 mM formamidine acetate and 0.05% Hamposyl™ C (·), but controls were not treated (▽). Each data point is the mean of 3 separate measurements. The line representing treated plants is a linear regression and the line representing controls is a binomial regression.

FIG. 10 shows the relationship between assimilation and transpiration. Measurements of the assimilation/transpiration (A/T) ratio in cabbage leaves treated with a

TABLE 5

Effect of enhancers, $C_1$-acceptor compounds and $C_1$-inputs on $CO_2$ Gas Exchange

| Treatment | | Species | Assimilation (Treatment/Control) (h after treatment) | | n |
|---|---|---|---|---|---|
| | | | 24 | 48 | |
| Folinate | 0.02 mM | Soy | 2.86 ± 1.08 | 1.65 ± 0.44 | 8 |
| Folinate | 0.09 mM | Sunflower | 1.34 ± 0.20 | — | 3 |
| Folate | 0.11 mM | Cabbage | 2.49 ± 1.1 | 1.31 ± 0.12 | 2 |
| pABA | 0.50 mM | Cabbage | 1.16 ± 0.17 | 1.53 ± 0.13 | 6 |
| pABA | 0.07 mM | Kale | 1.01 ± 0.11 | 1.14 ± 0.11 | 3 |
| pABA | 0.15 mM | Kale | 0.94 ± 0.11 | 1.20 ± 0.01 | 3 |
| pABA | 0.29 mM | Kale | 1.09 ± 0.04 | 1.17 ± 0.11 | 3 |
| pNBA | 0.10 mM | Sunflower | 1.86 ± 0.42 | — | 2 |
| pFBA | 0.10 mM | Cabbage | 1.46 ± 0.56# | — | 6 |
| Uvinul ® | 0.50 mM | Cabbage | 1.34 ± 0.32 | 1.25 ± 0.06 | 6* |
| pAH | 0.50 mM | Soy | 1.08 ± 0.09 | 0.99 ± 0.07 | 8 |
| Benzocaine ™ | 0.06 mM | Kale | 1.09 ± 0.29 | 1.05 ± 0.06 | 3 |
| Benzocaine ™ | 0.12 mM | Kale | 1.04 ± 0.23 | 1.03 ± 0.01 | 3 |
| Benzocaine ™ | 0.24 mM | Kale | — | 1.02 ± 0.11 | 3 |
| FIGly | 2 mM | Cabbage | 1.65 ± 0.31 | 1.20 ± 0.23 | 6* |
| FIGly | 2 mM | Soy | 1.29 ± 0.9 | 1.17 ± 0.24 | 6* |
| FIGly | 2 mM | Sugar beet | 1.47 ± 0.08 | 1.29 ± 0.14 | 4§ |
| FAM | 30 mM | Sunflower | 1.23 ± 0.21 | — | 3 |
| FAM + GO | 30 mM | Sunflower | 1.22 ± 0.23 | — | 3 |
| MeOH | 5000 mM | Soy | 2.00 ± 0.5 | — | 6 |

*n = 3 for 24 h; § = 2 for 24 h; *72 h after 3rd spray; *24 h after 3rd spray.

Assimilation/Transpiration data yielded the following results given in Table 6, below, wherein reduced transpiration with increased $CO_2$ assimilation was recorded for treatment of foliage with folinate, pAH and MeOH.

TABLE 6

Effect of enhancers, $C_1$-acceptor compounds and $C_1$-inputs on A/T

| Treatment | | Species | Assimilation/Transpiration (Treatment/Control) (h after treatment) | | n |
|---|---|---|---|---|---|
| | | | 24 | 48 | |
| Folinate | 0.02 mM | Soy | 1.27 ± 0.12 | 1.46 ± 0.14 | 8 |
| pAH | 0.5 mM | Soy | 1.33 ± 0.17 | 0.92 ± 0.10 | 8 |
| MeOH | 5000 mM | Soy | 1.36 ± 0.21 | — | 6 |

Figure 7:
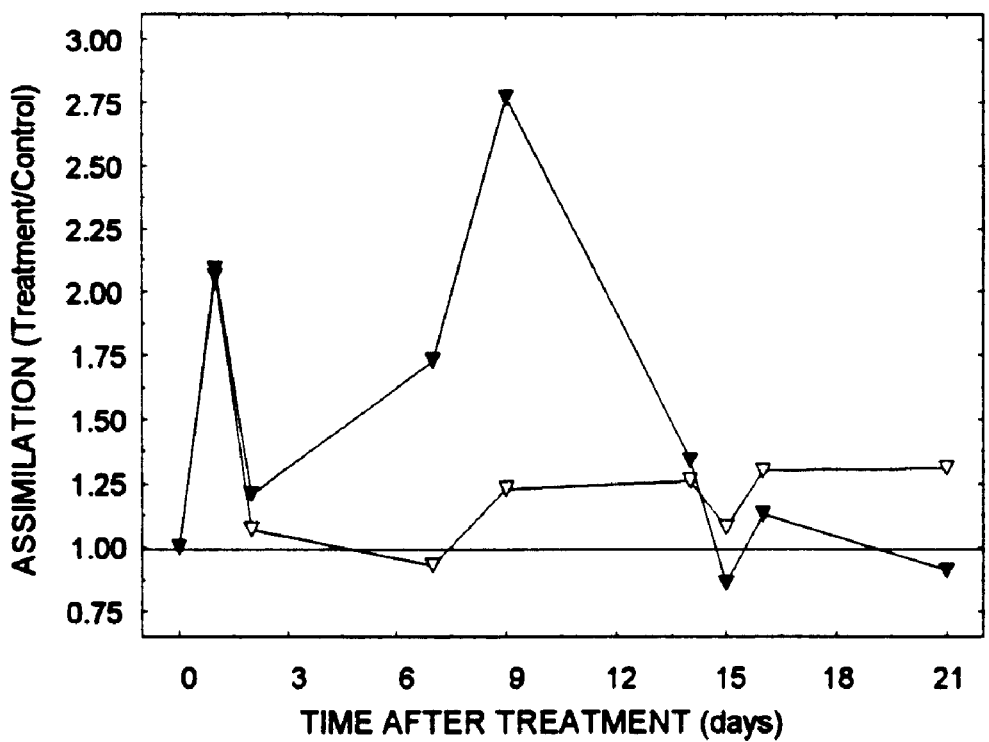
FIG. 7 is a graphic depiction showing the effects of folinate or methanol on long-term $CO_2$ gas exchange. Soy foliage was sprayed with 20 $\mu$M folinate, 40 mM glycine, 1% dimethylsulfoxide and 0.05% Hamposyl™ C (▼); or 5 M methanol, 40 mM glycine and 0.1% Triton® X-100 (▽). Each point is the mean of 3 to 8 measurements.

FIGS. 7, 8, 9 and 10 summarize results of the long-term effects of various treatments on gas exchange. FIG. 7 compares the effects of foliar sprays of 20 μM folinate to 5 M MeOH and showing increased $CO_2$ gas exchange over soy controls lasting three weeks. Plants were treated at the start and at 120 h. Peak activity was observed during the first and second weeks, the response to folinate far exceeding responses to MeOH. Each data point in this graph is the mean of samples such that two different leaves were measured on individual plants; for folinate, n=16 except on days 9, 15, 16 and 21 when n=8; for MeOH, n=8 except on days 9, 15, 16 and 21 when n=6; and for the control, n=12 on days 9, 15, 16 and 21 when n=16.

formulation containing 30 mM FAM showed $CO_2$ assimilation maintained with reduced transpiration for the duration of the experiment.

Generally, gas exchange increases were observable several hours after treatment. For example, within the first 2 to 3 h of application, no significant difference in gas exchange was noted in soy foliage treated with folinate; but after 6 h, the same leaves showed elevated gas exchange rates as compared to controls that were not treated. After 6 h, the average overall increase in gas exchange on folinate treated plants was approximately 35% greater than in controls. Three weeks after treatment, increased gas exchange was still observed. When treatments were repeated once per week, increased gas exchange continued to the termination of the study at one month. Treatment with pABA required more time to show increases in gas exchange than most other compounds. Generally, sometime after 24 h and within 48 hours, pABA treatments showed an increase in gas exchange over controls.

The effects of treatments on the quantity of the $C_1$-THF pool of leaves are given in Table 7, below. Treatments with MeOH, FIGly and folinate significantly increased the total $C_1$-THF pool and the $Glu_n$ chains over controls. Short-chained pteroyls increased significantly over controls when treated by 0.1 mM folinate, but not by MeOH or FIGly. Overall, folinate was a more effective enhancer of the $C_1$-THF pool than MeOH or FIGly. Treatments with 10 mM FIGly and 14.8 M MeOH showed equivalent increases in the total $C_1$-THF pool; this result underscoring the increased quantities of MeOH required to achieve the same responses as those observed for treatments with small quantities of FIGly or even more minute quantities of folinate. These increases in the $C_1$-THF pool corresponded closely to increased photosynthetic gas exchange and enzymes measured at the time of sampling.

following folinate with glycine in the sun resulted in turgid foliage. Post-folinate additions of glycolate with glycine were repeatable daily or as infrequently as once in three weeks. The practical nontoxic concentrations of glycolate and glycine are limited by penetration prior to evaporation of the water. Following folinate treatments, when used in the field under direct sunlight, only glycine supplementation was required because the plants were continuously producing glycolate from photorespiration within the leaf.

TABLE 7

Effect of Treatments on the $C_1$-THF Pool

| Treatment | | | Species | $C_1$-THF Pool (Treatment/Control) (± Standard deviation) | | | n |
|---|---|---|---|---|---|---|---|
| | | | | Short Chain Pteroyls | $Glu_n$ | Total $C_1$-THF Pool | |
| Folinate | 0.1 | mM | Sugar beet | 1.43 ± 0.15 | 1.28 ± 0.16 | 1.38 ± 0.04 | 3 |
| FIGly | 10 | mM | Sugar beet | 1.04 ± 0.06 | 1.39 ± 0.14 | 1.17 ± 0.04 | 3 |
| MeOH | 14,800 | mM | Sugar beet | 0.90 ± 0.08 | 1.74 ± 0.16 | 1.17 ± 0.06 | 3 |

In our test of water stress, after plants were rewatered, we observed that the plants treated with folinate survived the drought, whereas the shoots of all controls withered and died. Pretreatment of plants with folinate followed by post-treatment with glycolate and glycine improved turgidity of the plants in shade. Treatments with 40 mM glycolate or 40 mM glycine alone did not improve turgidity in the shade or in sunlight. Plants that were treated with 40 mM glycolate and exposed to direct sunlight were dead within a week. Plants under direct sunlight that were treated with 40 mM glycolate immediately followed by applications of 40 mM glycine showed healthy leaves with no phytotoxicity observed within a month. Folinate followed by 40 mM glycolate treatments in the sun resulted in wilt, whereas, Foliar treatments with solutions containing folinate, Uvinul® P-25, pABG, pNBA, DNBA, CNBA, NCBA, 2ClBA, CBA, CBG, pteroic acid, FIGly, pAH, pFBA, FAF or glycolate enhanced growth as compared to controls, shown in Table 8. No growth improvements were observed for Benzocaine™ and MeoABA. Corn showed growth improvement by treatment with nitrobenzoates and folinate.

TABLE 8

Effect of Treatments on Plant Growth

| Compound(*) | ppm | Plant | Fresh Wt. | | Dry Wt. | |
|---|---|---|---|---|---|---|
| | | | (g/10 plants) | (%) | (mg/10 plants) | (%) |
| Control | | All Plants | | 100 | | 100 |
| Folinate (C) | 50 | Radish | 2.38 | 138 | 150 | 131 |
| | 50 | Rice | 1.68 | 115 | 260 | 129 |
| | 50 | Corn | 11.9 | 105 | 760 | 104 |
| Folinate + $GO^{1X}$(B) | 7 + 2000 | Wheat | 0.23 | 134 | 31 | 141 |
| Folinate + $GO^{2X}$(B) | 7 + 2000 | Wheat | 0.25 | 148 | 33 | 150 |
| Pteroic (B) | 15 | Radish | 1.29 | 115 | 70 | 110 |
| pABG (C) | 100 | Radish | 0.90 | 111 | 60 | 119 |
| | 100 | Wheat | 4.54 | 121 | 38 | 123 |
| | 100 | Rice | 1.72 | 124 | 26 | 136 |
| pAH (B) | 25 | Radish | 1.57 | 115 | 90 | 113 |
| Uvinul ® (D) | 1265 | Radish | 1.08 | 157 | 60 | 150 |
| pNBA (A) | 7 | Radish | 1.59 | 173 | 110 | 179 |
| (B) | 7 | Corn | 1.28 | 111 | 890 | 119 |
| DNBA (B) | 212 | Radish | 1.35 | 114 | 90 | 113 |
| CNBA (B) | 15 | Radish | 1.09 | 131 | 60 | 141 |
| NCBA (B) | 30 | Radish | 0.90 | 161 | 60 | 177 |
| 2ClBA (B) | 10 | Radish | 1.17 | 114 | 62 | 119 |
| CBA (B) | 17 | Radish | 1.28 | 138 | 76 | 135 |
| CBG (B) | 28 | Radish | 1.17 | 131 | 70 | 134 |
| pFBA (B) | 15 | Radish | 1.26 | 102 | 70 | 106 |
| pFBA (B) | 75 | Soy Bean** | 1.21 | 112 | 211 | 119 |
| MeoABA (B) | 100 | Wheat | 3.67 | 95 | 340 | 99 |
| FIGly (B) | 500 | Radish | 1.20 | 110 | 70 | 114 |
| | 51 | Wheat | 3.74 | 121 | 350 | 130 |
| FAF (B) | 10 | Radish | 0.84 | 112 | 51 | 106 |
| GO (B) | 5000 | Wheat | 4.34 | 162 | 510 | 146 |

TABLE 8-continued

Effect of Treatments on Plant Growth

| Compound(*) | ppm | Plant | Fresh Wt. (g/10 plants) | (%) | Dry Wt. (mg/10 plants) | (%) |
|---|---|---|---|---|---|---|
| HAMPOSYL ™ (D) | 160 | Wheat | 1.15 | 85 | 170 | 87 |
| Glycine (D) | 2000 | Wheat | 1.06 | 80 | 160 | 85 |

*Active components were formulated in the following control solutions: (A) 0.05% HAMPOSYL ™ C surfactant, (B) 0.2% glycine + 0.05% HAMPOSYL ™ C, (C) 200 ppm potassium formate + 0.2% glycine + 0.05% HAMPOSYL ™ C, and (D) water. Folinate was followed by $GO^{1X}$ once at 2 d or $GO^{2X}$ twice at 2d and 4d.
**Bean yield was measured at University of Wyoming.

The treatments given in Table 8 were selected from a broad range of concentrations of each formulation that was applied and represent optimal doses for growth improvement in each case. The most effective concentration is directly related to the volume of solution applied, therefore, the actual concentration must be adjusted according to the quantity absorbed into foliage.

Discussion

The $C_1$-THF pool was substantially enhanced by our plant treatments. Foliar applications of $\mu$M to mM quantities of substances such as folinate, substituted benzoates and pteridines that appear to contribute to the $C_1$-THF structure increased rates of $CO_2$ fixation, sugar, photosynthetic gas exchange, $C_1$-THF enzymes, $C_1$-THF and water use efficiency. The improved physiology and biochemistry we observed was directly correlated to improved growth of green plants that we tested. Furthermore, enhancement of $C_1$-THF followed by $C_1$-input pulses or by continuous exposure to $O_2$-Uptake, plant growth improved for long durations. We conclude that enhancement of $C_1$-THF increases the efficiency of carbon fixation into plant growth. Our studies show that yield improvement over the long-term is consistent with immediate visual assays of turgidity, instrumental measures of gas exchange, and biochemical determinations of $C_1$-THF enzyme stimulation. Supplanting our growth assay with enzyme and photosynthetic analyses, thereby, reduced our surveys from months to hours, allowing rapid adjustment of formulations.

The general biochemistry of photosynthesis and photorespiration has been reviewed (e.g., Andrews and Lorimer 1987; Ogren 1984), but methods for applying biochemical pathways to substantially reduce photorespiration, increase carbon fixation and improve water use efficiency has never previously been cited. Our pulse-chase studies clearly show that our treatments with enhancers or $C_1$-inputs increased the rate of $CO_2$ fixation followed by rapid metabolism to sugar. The trend towards the magnificent increase of glycine:serine ratios we observed in plants treated with methanol, p-aminobenzoylglutamate or folinate over controls implies unusually rapid transport of serine out of the mitochondria to the cytosol. Rapid transport is supported by our data, i.e., our pulse-chase measures show evidence of serine→phosphoglyceric acid→sugars. We conclude that enhancers caused heightened rates and quantities of carbon fixation to sugars and other cellular constituents beneficial to growth.

Compounds that contribute components to the molecular structure of $C_1$-THF either in large portions (e.g., by application of folinate, pteroic acid or benzoates) or via carbon fragments (e.g., by application of formate, oxalate or glyoxylate) are suitable for enhancing photosynthetic productivity for long durations when a source of $Glu_n$ is provided. Studies on the effects of different photorespiratory metabolites on photosynthesis have been aimed at determining pathways and sources of carbon released during photorespiration in isolated tissues. It has been shown that changing the concentration of some common metabolites, such as L-glutamate, L-aspartate, phosphoenolpyruvate and glyoxylate decreases the amount of photorespiration and increases net photosynthesis (Oliver & Zelitch 1977a). Experiments were carried out on low-light grown plants (300 $\mu$mol photosynthetically active quanta $m^{-2}s^{-1}$, 21° C.).

Glycolate accumulation was assayed in leaf discs floated on aqueous solutions at 0.39 mmol photosynthetically active quanta $m^{-2}s^{-1}$ and 30° C. These conditions are not necessarily photoinhibitory, but glycolate synthesis was apparently decreased in the leaf discs treated with 30 mM L-glutamate (Oliver & Zelitch 1977b). Inhibition of photosynthesis caused by accumulation of glycolate has been reported (Ogren 1984; Wendler et al. 1992; Zelitch 1978) and it is generally accepted that glycolate must be further metabolized, otherwise, it is detrimental to photosynthesis. Formate feeding to plants has been used to determine how formate is metabolized (Tolbert 1955; Tolbert 1981). The concentration of formate used was not given, but it was applied through the transpirational stream, i.e., the cut edge of detached leaves were placed in aqueous solutions containing the labeled formate. Other studies (e.g., Hiatt 1965) in higher plants were carried out with leaf slices in aqueous solutions with $\mu$M formate concentrations. Growth increased according to carbon fertilization as was demonstrated in our applications of folinate followed by glycolate applications either once or twice within four days. We conclude that improving the fixation of carbon followed by carbon nutriment increases growth substantially more than has been possible by application of conventional fertilizers alone.

Of the specific enzymes involved in $C_1$-THF transport of carbon (Cossins et al. 1993), our assays showed increases of $C_1$-THF-synthase, 10-formyl-THF-synthetase, 5,10-methenyl-THF-cyclohydrolase and 5,10-methylene-THF-dehydrogenase in foliage treated with enhancers and $C_1$-inputs, serving as rapid verification of their involvement in plant growth by stimulation of enzymes.

Treatments with enhancers or $C_1$-inputs resulted in increased turgor suggesting greater rates of photosynthesis related to favorable stomatal aperture. With closed stomata, the internal $CO_2$ would decrease to the $CO_2$ compensation point, about 30–40 ppm in $C_3$ plants, and as low as 4 ppm in $C_4$ plants (Wu et al. 1991) and net photosynthesis is nil. Enhancement of $C_1$-THF can reduce transpiration, but contrary to the expected reduction of photosynthesis with application of conventional antitranspirants that act by completely blocking stomata, we discovered that application of enhancers or $C_1$-inputs maintains carbon dioxide assimilation with reduction of transpiration. Multiple foliar pools exchange sucrose and regulate stomata (Outlaw 1995) based on photosynthesis. Evidenced by our pulse-chase investigations, high Assimilation/Transpiration ratios caused by our treatments is most likely related to just such enhancement of sucrose in the leaves. Thus, contrary to conventional trends in plant physiology and much to our surprise, reduction of transpiration can benefit plant growth and improve water use efficiency.

It is probable that the increased carbon-based growth we have observed is related to the catalytic nature of vitamins we applied. The vitamins utilized in these studies are involved in catalysis of $C_1$ transport. The very low concentrations of the vitamins at which we found response suggest high potency. Key to prolonged improved photosynthesis may have been efficient penetration of the $\mu M$ concentrations of vitamins that we applied. Adding the penetrant DMSO enhanced the potency of folinate, clearly, pointing out the dependence of activity upon penetration of such large molecules. Significant plant growth response to Uvinul® P-25 formulations to which no surfactant was added is attributable to the penetrative characteristic of the polyethyleneglycol (PEG) chains attached to the pABA in the makeup of Uvinul® P-25. Ethoxylates of other active compounds such as pteroic acid, phthalates or nitrobenzoates would be useful for single component product formulations. Ethoxylating pABA has the additional benefit of improving the solubility of pABA in water thus characterizing ethoxylation as an Activator. Salts, such as, calcium folinate, are water soluble; furthermore, in view of its reduced state, folinate has long been considered the activated form of vitamin M (Merck Index, monograph #4111).

Contributors to the $C_1$-THF pool that we now know to increase $C_1$ metabolism may modulate the flow of carbon through the $C_3$ cycle. $C_1$-THF is present in fungal spores and can originate nonenzymatically from 5,10-methenyl-THF. A futile cycle in the fungus *Neurospora crassa* exists, in which, rather than rapidly contributing to the flow of carbon, $C_1$-THF binds tightly to serine hydroxymethyltransferase-glycine which further inhibits methenyl-THF-synthetase and other enzymes downstream (Stover et al. 1993; Kruschwitz et al. 1994) limiting the supramolecular ternary complex to a slow release of its contents. $C_1$-THF-dependent enzymes bind $C_1$-THF in pea foliage (Besson et al. 1993) and it is likely that catalysis by ternary complexes similar to those found in *Neurospora crassa* would explain the long-duration effect that we have observed in our studies. The $Glu_n$ stored in the $C_1$-THF pool may be released over several days or weeks depending on demands to maintain equilibrium during photorespiration. Regulation of photorespiration may be determined according to maintenance of high flows of $C_1$ fragments, an equilibrium that can benefit growth with maintenance of high glycine:serine ratios. In our studies, it is possible that appreciable quantities of glycine were separated from the serine hydroxymethyltransferase·glycine·pteroylpolyglutamate ternary complex during processing of our samples for chromatographic separations, our data thus fitting this pathway. In our studies of the $C_1$-THF pool, when FIGly was used, the greatest increase was observed in the portion of the pteroyl-$Glu_n$ pool having the long chain $Glu_n$ residues. Increase of short-chained $Glu_n$ pteroyls was less. This is likely related to the very high level of $Glu_n$ source in the structure of FIGly. In contrast, folinate, which based on its structure, is likely to make a much greater contribution to the pteroyl portion than FIGly and a lower contribution to the $Glu_n$ portion, exhibited a higher level of short chain $Glu_n$ pteroyl enhancement as compared to the long chain $Glu_n$ enhancement. Our results, therefore, show the importance of contributing to the entire $C_1$-THF pool, by combining enhancers, $C_1$-inputs and $C_1$-acceptors into a single formulation.

The $\mu M$ quantities of folinate or substituted benzoates applied to plants in our studies are far greater than the nanomolar quantities normally found in foliage and should provide adequate stores for cell cycles even in the face of limited penetration. With efficient penetration of these substances, serine hydroxymethyltransferase may be activated to bind the input, thus, necessitating inputs aimed at lengthening the $Glu_n$ chain. In order to maintain very high flows of $C_1$ fragments, the $C_3$ cycle might be diverted from the GOGAT cycle. Specifically, decarboxylation of glyoxylate has been shown (e.g., Grodzinski 1978; Zelitch 1972) where glycolate from the $C_3$ cycle can be broken down to carbon dioxide and formate. Passage of fragments from glycolate through 10-formyl-THF in the $C_1$ pathway may, thus, occur. The existence of such alternate pathways leads us to speculate that treatment of foliage with compounds such as folinate that we now know to increase $C_1$ metabolism, may do so by influencing photorespiration. On the surface, because corn is a $C_4$ plant with limited photorespiration and since we observed increases in growth and stimulation of enzymes after treatments of corn with pNBA and folinate, reduction of photorespiration might not seem to be the case; however, the low levels of growth improvement that we measured for these treatments are in order with the complete correction of the low levels of photorespiration typical of corn.

Recent studies on transformation of nitroaromatics by bacteria (Gorontzy et al. 1993) and on chloramphenicol in rats (de Vries et al. 1994) established that substituted benzoates can be metabolized to their aminobenzoic acid derivatives. Schackmann and Muller (1991) proposed a pathway for reduction of nitroaromatic compounds in bacteria by which the reaction to the aminoaromatic derivative occurs in stepwise reductions, for example, from p-nitrobenzoic acid to p-nitrosobenzoic acid to p-hydroxylaminobenzoic acid to p-aminobenzoic acid. In plants, $C_1$-THF appears to similarly catalyze detoxification. Substitutions at the 2, 3 and/or 4 positions of the benzene ring showed the highest activity in our plants, and, given the likelihood that all of our substituted aromatics are metabolized into $C_1$-THF, active combinations of amino-, nitro-, formyl-, phthaloyl-, sulfo-, sulfamyl-, and halide moieties are numerous. The wide range of possible denitrifying compounds suggests the potential for use of crops with enhanced $C_1$-THF as a means of detoxifying environments polluted with nitroaromatics such as trinitrotoluene.

As highly available nitrogen sources, $C_1$-acceptor compounds prevent some problems inherent with the use of classical nitrogen sources combined with our proposed carbon sources. When nitrogen contributions of a $C_1$-acceptor compound are balanced with appropriate $C_1$ sources, such as we observed in our experiments with glycolate and glycine, toxic concentrations become beneficial to growth and enhance carbon fixation. We have discovered that formamidines are excellent sources of nitrogen for plants, but without the toxicity of biuret, for example, associated with urea fertilizers.

This technology has beneficial potential for recombinant DNA technology. Since formate induced $C_1$-THF-synthetase in *Micrococcus aerogenes* (Whiteley et al. 1959), we were not surprised to observe the induction of this complex of enzymes in plants that we treated. Specific $C_1$-THF's function in the synthesis of thymidylate, purines and histidine for production of new DNA and RNA which is necessary for the creation of new cells/growth. Formyltetrahydrofolate acts on initiation of protein synthesis in Prokaryotes. The formyl-group in purine synthesis may be from methenyltetrahydrofolate, perhaps, originating from formate or glycolate. Attachment of a $C_1$ fragment to homocysteine via methyltetrahydrofolate yields methionine and its derivatives, such as S-adenosylmethionine, which are essential to all protein syntheses. Plants could be genetically altered or classically bred for increased levels of the enzymes associated with such $C_1$-THF functions. If the enzymes involved in the $C_1$ pathway (Cossins 1980; 1987) can be altered, adjusted, or over-expressed to give long-term results similar to our vitamin treatments, then plants so altered should have increased water use efficiency and productivity.

Based on the results of our biochemistry, physiology and growth studies, we conclude that our treatments of plants designed to enhance the $C_1$-THF pool cause increases in the rate and quantity of carbon fixation and provide practical methods for carbon fertilization. Our discovery provides processes for achieving water use efficiency while gaining ever greater photosynthetic productivity for all plants.

Literature Cited in Experimental Section

Andrews, T. J. and G. H. Lorimer, 1987. In M. D. Hatch and N. K. Boardman, Eds. The Biochemistry of Plants: A Comprehensive Treatise, Vol. 10, Academic Press, San Diego, Pp 131–218.

Besson, V., F. Rebeille, M. Neuburger, R. Douce and E. A. Cossins. 1993. Effects of tetrahydrofolate polyglutamates on the kinetic parameters of serine hydroxymethyltransferase and glycine decarboxylase from pea leaf mitochondria. Biochem. J. 292:425–430.

Cossins, E. A. 1964. The utilization of carbon-1 compounds by plants. Can. J. Biochem. 42:1793–1802.

Cossins, E. A. 1980. One-Carbon Metabolism. In The Biochemistry of Plants, v. 2, P. K. Stumph & E. E. Conn, Eds., Academic Press, NY, Pp.365–418.

Cossins, E. A. 1987. Folate Biochemistry and the Metabolism of One-Carbon Units. In The Biochemistry of Plants, v. 11, D. D. Davies, Ed., Academic Press, NY, Pp.317–353.

Cossins, E. A., C. D. Kirk, H. C. Imeson and L. Zheng. 1993. Enzymes for synthesis of 10-formyltetrahydrofolate in plants. Characterization of a monofunctional 10-formyltetrahydrofolate synthetase and copurification of 5,10-methylenetetrahydrofolate dehydrogenase and 5,10-methenyltetrahydrofolate cyclohydrolase activities. In Chemistry and Biology of Pteridines and Folates, J. E. Ayling, M. G. Nair and C. M. Baugh, Eds., Plenum Press, NY, Pp 707–710.

Crosti, P., M. Malerba and R. Bianchetti. 1993. Growth-dependent changes of folate metabolism and biosynthesis in cultured *Daucus carota* cells. Plant Science (Limerick) 88(1):97–106.

de Vries, H., P. J. Hemelaar, A. C. J. Gevers and G. M. J. Beyersbergen van Henegouwen. 1994. Photoreactivity of Chloramphenicol in vitro and in vivo. Photochem. and Photobiol. 60:249–252.

Gorontzy, T., J. Kuver and K. H. Blotevogel. 1993. Microbial transformation on nitroaromatic compounds under anaerobic conditions. J. Gen. Microbiology 139:1331–1336.

Grodzinski, B. 1978. Glyoxylate decarboxylation during photorespiration. Planta 144:31–37.

Hiatt, A. J. 1965. Formic Acid Activation in Plants. I. Purification, Properties and Distribution of Formyltetrahydrofolate Synthetase. Plant Physiol. 40:184–188.

Ogren, W. L. 1984. Photorespiration: pathways, regulation, and modification. Ann. Rev. Plant Physiol. 35:415–442.

Oliver, D. J. and I. Zelitch. 1977a. Metabolic regulation of glycolate synthesis, photorespiration, and net photosynthesis in tobacco by L-glutamate. Plant Physiol. 59:688–694.

Oliver, D. J. and I. Zelitch. 1977b. Increasing photosynthesis by inhibiting photorespiration with glyoxylate. Science 196:1450–1451.

Outlaw, W. H. 1995. Stomata and Sucrose: A Full Circle. In Carbon Partitioning and Source-sink Interactions in Plants, Current Topics in Plant Physiology: An American Society of Plant Physiologists Series, v. 13, M. A. Madore and W. J. Lucas, eds., The American Society of Plant Physiologists, Rockville, Md., Pp 56–67.

Schackmann, A. and R. Muller. 1991. Reduction of aromatic compounds in different Pseudomonas species under aerobic conditions. Appl. Microbiol. Biotechnol. 34:809–813.

Stover, P., H. Kruschwitz and V. Schirch. 1993. Evidence that 5-formyltetrahydropteroylglutamate has a metabolic role in one-carbon metabolism. In Chemistry and Biology of Pteridines and Folates, J. E. Ayling, M. G. Nair and C. M. Baugh, Eds., Plenum Press, NY, Pp 679–685.

Tolbert, N. E. 1955. Formic acid metabolism in barley leaves. J. Biol. Chem. 215:27–34.

Tolbert, N. E. 1981. Metabolic pathways in peroxisomes and glyoxisomes. *Ann. Rev. Biochem.* 50:133–157.

Wendler, C., A. Putzer, A. Wild. 1992. Effect of glufosinate (phosphinothricin) and inhibitors of photorespiration on photosynthesis and ribulose-1,5-bisphosphate carboxylase activity. J. Plant Physiol. 139:666–671.

Whiteley, H. R., M. J. Osborn and F. M. Huennekens. 1959. Purification and properties of the formate-activating enzyme from *Micrococcus aerogenes*. J. Biol. Chem. 234:1538–1543.

Wu, J., S. Neimanis, U. Heber. 1991. Photorespiration is more effective than the Mehler reaction in protecting the photosynthetic apparatus against photoinhibition. Bot. Acta 104:283–291.

Zelitch, I. 1972. The photooxidation of glyoxylate by envelope-free spinach chloroplasts and its relation to photorespiration. Arch. Biochem. Biophys. 150:698–707.

Zelitch, I. 1978. Effect of glycidate, an inhibitor of glycolate synthesis in leaves, on the activity of some enzymes of the glycolate pathway. Plant Physiol 61:236–241.

Although the foregoing invention has been described in detail for purposes of clarity of understanding, it will be obvious that certain modifications may be practiced within the scope of the appended claims.

All patents, patent applications and publications cited in this application are hereby incorporated by reference in their entirety for all purposes to the same extent as if each individual patent, patent application or publication were so individually denoted.

What is claimed is:

1. A method of promoting growth of a plant, said method comprising:
   (a) applying to leaves of the plant an amount of an enhancer substance which increases the amount of $C_1$-tetrahydrofolate ($C_1$-THF) in the leaves; and
   (b) applying to the leaves a $C_1$-input substance selected from the group consisting of formamidine salts of carboxulic acids and formimino amino acids, which increases the metabolism of $C_1$ fragments through $C_1$-THF and a $C_1$-acceptor compound which serves a sink for $C_1$ fragments in the leaves.

2. The method of claim 1, wherein the enhancer is selected from the group consisting of $C_1$-THF compounds, pteridines, pterins, pteroic acids, pteroyl compounds, folinates, substituted benzoic acids, substituted benzoates and derivatives thereof; and salts, hydrates and surfactant-linked derivatives thereof, applied as an aqueous solution at a concentration in the range from about 0.0001% by weight to 0.5% by weight.

3. The method of claim 2, wherein the enhancer is a pteridine of the formula below, wherein:

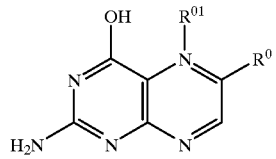

$R^{01}$ is hydrogen or is a hydrocarbyl group capable of being metabolized to a one carbon substituent having the oxidation state of a methyl, hydroxymethyl, formyl or formic acid residue; and $R^0$ is independently selected from the group consisting of:
methylene-aminobenzoate, optionally substituted on the benzoate ring;
methylene-aminobenzoyl(Glu)$_n$, wherein n is an integer from 0 to 10, optionally substituted on the benzoyl ring; and
its corresponding dihydro- and tetrahydro-reduction products at positions 5, 6, 7, and/or 8 of the pteridine ring; and salts, hydrates and surfactant-linked derivatives thereof, applied as an aqueous solution at a concentration in the range from about 0.0001% by weight to 0.5% by weight.

4. The method of claim 1, wherein the enhancer is in a solution comprising an activator substance selected from the group consisting of alcohols, organic nitrogenous bases, alkali metal hydroxides, alkaline earth metal hydroxides, hydrocarbyl acids and surfactants.

5. The method of claim 6, wherein the enhancer is a $C_1$-THF compound selected from the group consisting of folinic acid, anhydroleucovorin, 5-formyltetrahydropteroyl polyglutamate, 10-formyltetrahydropteroyl polyglutamate, 5-formyltetrahydrofolate, 10-formyltetrahydrofolate, 5-methyltetrahydrofolate, 10-methyltetrahydrofolate, 5,10-methenyltetrahydrofolate and 5,10-methylenetetrahydrofolate; and salts, hydrates and surfactant-linked derivatives thereof, applied as an aqueous solution at a concentration in the range from 0.0001% by weight to 0.5% by weight.

6. The method of claim 1, wherein the enhancer is p-nitrobenzoic acid, and the $C_1$-acceptor compound is a urea.

7. The method of claim 1, wherein the enhancer is terephthalic acid, and the $C_1$-acceptor compound is glycine.

8. The method of claim 1, wherein the enhancer is calcium folinate, and the $C_1$-acceptor compound is hexamethylenetetramine.

9. The method of claim 1, wherein the enhancer is m-nitrobenzoic acid, and the $C_1$-acceptor compound is acylglycine.

10. The method of claim 1, wherein the enhancer is PEG-p-nitrobenzoate, and the $C_1$-acceptor compound and $C_1$-input is formamidine glycolate.

11. A plant growth promoting system comprising:
a first aqueous solution or a nonaqueous material which when combined with an aqueous carrier contains an amount of a $C_1$-acceptor compound effective to serve as a sink for $C_1$ fragments in leaves of a plant when applied to leaves of the plant; and
a second aqueous solution or a nonaqueous material which when combined with an aqueous carrier contains an amount of an enhancer substance effective to increase the amount of $C_1$-tetrahydrofolate ($C_1$-THF) in leaves of the plant when applied to the leaves of the plant and containing a $C_1$-input substance selected from the group consisting of formamidine salts of carboxylic acids and formimino amino acids, which increases the metabolism of $C_1$ fragments through $C_1$-THF when applied to the leaves of the plant.

12. The system of claim 11, wherein the enhancer is selected from the group consisting of $C_1$-THF compounds, pteridines, pterins, pteroic acids, pteroyl compounds, folinates, substituted benzoic acids, substituted benzoates and derivatives thereof; and salts, hydrates and surfactant-linked derivatives thereof.

13. The system of claim 12, wherein the enhancer is a pteridine of the formula below, wherein:

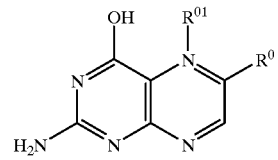

$R^{01}$ is hydrogen or is a hydrocarbyl group capable of being metabolized to a one carbon substituent having the oxidation state of a methyl, hydroxymethyl, formyl or formic acid residue; and $R^0$ is independently selected from the group consisting of:
methylene-aminobenzoate, optionally substituted on the benzoate ring;
methylene-aminobenzoyl(Glu)$_n$, wherein n is an integer from 0 to 10, optionally substituted on the benzoyl ring, and its corresponding dihydro- and tetrahydro-reduction products at positions 5, 6, 7, and/or 8 of the pteridine rings; and salts, hydrates and surfactant-linked derivatives thereof.

14. The system of claim 12, wherein the enhancer is a $C_1$-THF compound is selected from the group consisting of folinic acid, anhydroleucovorin, 5-formyltetrahydropteroyl polyglutamate, 10-formyltetrahydropteroyl polyglutamate, 5-formyltetrahydrofolate, 10-formyltetrahydrofolate, 5-methyltetrahydrofolate, 10-methyltetrahydrofolate, 5,10-methenyltetrahydrofolate and 5,10-methylenetetrahydrofolate; and salts, hydrates and surfactant-linked derivatives thereof.

15. A mixture for promoting growth of a plant comprising an aqueous solution or a nonaqueous material which when combined with an aqueous carrier contains p-nitrobenzoic acid, a formamidine salt of a carboxylic acid and agronomically suitable additives.

16. The mixture of claim 15, wherein the formamidine salt is formamidine glycolate.

17. The mixture of claim 15, wherein the formamidine salt is formamidine formate.

18. A mixture for promoting growth of a plant comprising an aqueous solution or a nonaqueous material which when combined with an aqueous carrier contains folinic acid, a formamidine salt of a carboxylic acid and agronomically suitable additives.

19. The mixture of claim 18, wherein the formamidine salt is formamidine glycolate.

20. The mixture of claim 18, wherein the formamidine salt is formamidine formate.

21. A mixture for promoting growth of a plant comprising an aqueous solution or a nonaqueous material which when combined with an aqueous carrier contains formamidine glycolate and agronomically suitable additives.

* * * * *